US012649048B2

(12) United States Patent     (10) Patent No.:   US 12,649,048 B2

Gilbert et al.           (45) Date of Patent:     Jun. 9, 2026

---

(54) CATHETER INSERTION DEVICES

(71) Applicant: St. Jude Medical, Cardiology Division, Inc., St. Paul, MN (US)

(72) Inventors: Therese Claire Gilbert, St. Paul, MN (US); Timothy Marass, Minneapolis, MN (US); Andrew Oliverius, Eagan, MN (US); Nicholas Strom, Minneapolis, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 18/467,049

(22) Filed: Sep. 14, 2023

(65) Prior Publication Data

US 2024/0108863 A1     Apr. 4, 2024

Related U.S. Application Data

(63) Continuation of application No. 15/790,601, filed on Oct. 23, 2017, now Pat. No. 11,786,705.

(Continued)

(51) Int. Cl.
    *A61M 25/09*       (2006.01)
    *A61M 25/01*       (2006.01)
    (Continued)

(52) U.S. Cl.
    CPC ...... *A61M 25/09041* (2013.01); *A61M 25/01* (2013.01); *A61M 25/0113* (2013.01);
    (Continued)

(58) Field of Classification Search
    CPC .......... A61M 25/0028; A61M 25/0029; A61M 25/003; A61M 25/0032; A61M 25/005;
    (Continued)

(56) References Cited

U.S. PATENT DOCUMENTS

| | | |
|---|---|---|
| 3,618,614 A | 11/1971 | Flynn |
| 3,825,036 A | 7/1974 | Stent |

(Continued)

FOREIGN PATENT DOCUMENTS

| | | |
|---|---|---|
| CN | 101927053 B | 1/2015 |
| CN | 103157168 B | 4/2015 |

(Continued)

OTHER PUBLICATIONS

"Cylindrical", Lexico, Available Online at: https://www.lexico.com/en/definition/cylindrical, Oct. 5, 2019, 4 pages.

*Primary Examiner* — Kami A Bosworth
(74) *Attorney, Agent, or Firm* — Kilpatrick Townsend & Stockton LLP

(57)          ABSTRACT

Various embodiments of the present disclosure provide a medical device straightener. The medical device straightener can comprise an elongate shaft extending along a shaft longitudinal axis, the elongate shaft including a shaft proximal end and a shaft distal end, wherein a shaft inner wall of the elongate shaft defines a shaft lumen extending therethrough. The medical device straightener can comprise a bleedback valve that includes an outer circumferential surface. The bleedback valve can be disposed at a distal end of the elongate shaft, within the shaft lumen, wherein a portion of the outer circumferential surface is in communication with the shaft inner wall. The bleedback valve can define a radially expandable lumen longitudinally extending through a center of the bleedback valve.

20 Claims, 16 Drawing Sheets

Related U.S. Application Data

(60) Provisional application No. 62/411,876, filed on Oct. 24, 2016.

(51) Int. Cl.

| | |
|---|---|
| *A61M 25/06* | (2006.01) |
| *A61M 25/00* | (2006.01) |
| *A61M 25/10* | (2013.01) |
| *A61M 39/06* | (2006.01) |

(52) U.S. Cl.
CPC .... *A61M 25/0606* (2013.01); *A61M 25/0693* (2013.01); *A61M 25/0028* (2013.01); *A61M 2025/0078* (2013.01); *A61M 25/0662* (2013.01); *A61M 2025/1056* (2013.01); *A61M 2039/062* (2013.01)

(58) Field of Classification Search
CPC ...... A61M 25/0075; A61M 2025/0004; A61M 2025/0006; A61M 2025/0076; A61M 2025/0078; A61M 2025/0681; A61M 2039/062
See application file for complete search history.

(56) References Cited

U.S. PATENT DOCUMENTS

| | | | |
|---|---|---|---|
| 4,932,413 A | | 6/1990 | Shockey et al. |
| 4,950,257 A | * | 8/1990 | Hibbs ............... A61M 25/0662 604/167.04 |
| 4,960,412 A | * | 10/1990 | Fink .................. A61M 39/0606 604/167.04 |
| 5,171,230 A | | 12/1992 | Eland et al. |
| 5,180,364 A | | 1/1993 | Ginsburg |
| 5,224,939 A | | 7/1993 | Holman et al. |
| 5,261,416 A | | 11/1993 | Taussig |
| 5,290,263 A | | 3/1994 | Wigness et al. |
| 5,380,301 A | | 1/1995 | Prichard et al. |
| 5,400,783 A | | 3/1995 | Pomeranz et al. |
| 5,456,254 A | | 10/1995 | Pietroski et al. |
| 5,626,136 A | | 5/1997 | Webster, Jr. |
| 5,715,817 A | | 2/1998 | Stevens-Wright et al. |
| 5,715,832 A | | 2/1998 | Koblish et al. |
| 5,776,115 A | | 7/1998 | Antoshkiw et al. |
| 5,792,116 A | | 8/1998 | Berg et al. |
| 5,807,328 A | | 9/1998 | Briscoe |
| 5,827,278 A | | 10/1998 | Webster, Jr. |
| 5,876,373 A | | 3/1999 | Giba et al. |
| 5,921,971 A | * | 7/1999 | Agro ................. A61M 25/0029 604/523 |
| 5,976,120 A | | 11/1999 | Chow et al. |
| 6,053,905 A | | 4/2000 | Daignault, Jr. et al. |
| 6,074,379 A | | 6/2000 | Prichard |
| 6,273,404 B1 | | 8/2001 | Holman et al. |
| 6,475,187 B1 | | 11/2002 | Gerberding |
| 6,491,681 B1 | | 12/2002 | Kunis et al. |
| 6,554,794 B1 | | 4/2003 | Mueller et al. |
| 7,004,937 B2 | | 2/2006 | Lentz et al. |
| 7,018,372 B2 | | 3/2006 | Casey et al. |
| 7,214,220 B2 | | 5/2007 | McGlinch et al. |
| 7,217,256 B2 | | 5/2007 | Di Palma |
| 7,534,250 B2 | | 5/2009 | Schaeffer et al. |
| 7,608,063 B2 | | 10/2009 | Le et al. |
| 7,625,365 B2 | | 12/2009 | McGlinch et al. |
| 7,666,204 B2 | | 2/2010 | Thornton et al. |
| 7,959,601 B2 | | 6/2011 | McDaniel et al. |
| 7,985,215 B2 | | 7/2011 | Guo et al. |
| 8,043,263 B2 | | 10/2011 | Helgeson et al. |
| 8,103,327 B2 | | 1/2012 | Harlev et al. |
| 8,137,321 B2 | | 3/2012 | Argentine |
| 8,221,390 B2 | | 7/2012 | Pal et al. |
| 8,273,016 B2 | | 9/2012 | O'Sullivan |
| 8,376,990 B2 | | 2/2013 | Ponzi et al. |
| 8,447,377 B2 | | 5/2013 | Harlev et al. |
| 8,608,703 B2 | | 12/2013 | Riles et al. |
| 8,636,714 B2 | | 1/2014 | McFerran |
| 8,649,880 B1 | | 2/2014 | Parker, Jr. |
| 8,700,120 B2 | | 4/2014 | Koblish |
| 8,706,193 B2 | | 4/2014 | Govari et al. |
| 8,755,861 B2 | | 6/2014 | Harlev et al. |
| 8,771,267 B2 | | 7/2014 | Kunis et al. |
| 8,777,929 B2 | | 7/2014 | Schneider et al. |
| 8,792,962 B2 | | 7/2014 | Esguerra et al. |
| 8,814,824 B2 | | 8/2014 | Kauphusman et al. |
| 8,814,825 B2 | | 8/2014 | Tegg et al. |
| 8,882,705 B2 | | 11/2014 | McDaniel et al. |
| 8,894,610 B2 | | 11/2014 | Macnamara et al. |
| 8,905,973 B2 | | 12/2014 | Tegg et al. |
| 8,979,841 B2 | | 3/2015 | Kunis et al. |
| 8,996,091 B2 | | 3/2015 | de la Rama et al. |
| 9,017,308 B2 | | 4/2015 | Klisch et al. |
| 9,033,917 B2 | | 5/2015 | Magana et al. |
| 9,050,010 B2 | | 6/2015 | Bui et al. |
| 9,101,733 B2 | | 8/2015 | McDaniel |
| 9,204,929 B2 | | 12/2015 | Solis |
| 9,216,056 B2 | | 12/2015 | Datta et al. |
| 9,247,990 B2 | | 2/2016 | Kauphusman et al. |
| 9,326,815 B2 | | 5/2016 | Watson |
| 9,339,631 B2 | | 5/2016 | Graham et al. |
| 9,427,562 B2 | | 8/2016 | Blacker |
| 9,433,751 B2 | | 9/2016 | Ponzi et al. |
| 9,433,752 B2 | | 9/2016 | Jimenez et al. |
| 9,468,495 B2 | | 10/2016 | Kunis et al. |
| 9,474,486 B2 | | 10/2016 | Eliason et al. |
| 9,486,280 B2 | | 11/2016 | Koblish et al. |
| 9,486,282 B2 | | 11/2016 | Solis |
| 9,522,035 B2 | | 12/2016 | Highsmith |
| 9,539,413 B2 | | 1/2017 | Ogle |
| 9,629,675 B2 | | 4/2017 | Kleshinski et al. |
| 9,649,158 B2 | | 5/2017 | Datta et al. |
| 9,687,166 B2 | | 6/2017 | Subramaniam et al. |
| 9,693,733 B2 | | 7/2017 | Altmann et al. |
| 9,694,159 B2 | | 7/2017 | Schneider et al. |
| 9,694,161 B2 | | 7/2017 | Selkee |
| 9,700,701 B2 | | 7/2017 | Benjamin et al. |
| 9,788,895 B2 | | 10/2017 | Solis |
| 9,820,664 B2 | | 11/2017 | Hoitink et al. |
| 9,844,645 B2 | | 12/2017 | Pai et al. |
| 9,848,795 B2 | | 12/2017 | Marecki et al. |
| 9,919,132 B2 | | 3/2018 | Tegg et al. |
| 9,949,656 B2 | | 4/2018 | Wu et al. |
| 9,986,949 B2 | | 6/2018 | Govari et al. |
| 10,004,877 B2 | | 6/2018 | Tegg |
| 10,034,637 B2 | | 7/2018 | Harlev et al. |
| 10,052,457 B2 | | 8/2018 | Nguyen et al. |
| 10,065,019 B2 | | 9/2018 | Hamuro et al. |
| 10,099,036 B2 | | 10/2018 | Heideman et al. |
| 10,118,022 B2 | | 11/2018 | Helgeson et al. |
| 10,136,829 B2 | | 11/2018 | Deno et al. |
| 10,143,394 B2 | | 12/2018 | Solis |
| 10,172,673 B2 | | 1/2019 | Viswanathan et al. |
| 10,258,771 B2 | | 4/2019 | Beissel et al. |
| 10,322,261 B2 | | 6/2019 | Pai et al. |
| 10,362,952 B2 | | 7/2019 | Basu et al. |
| 10,362,954 B2 | | 7/2019 | de la Rama et al. |
| 10,376,170 B2 | | 8/2019 | Quinn et al. |
| 10,384,036 B2 | | 8/2019 | Romoscanu |
| 10,398,500 B2 | | 9/2019 | Huszar et al. |
| 10,470,682 B2 | | 11/2019 | Deno et al. |
| 10,478,247 B2 | | 11/2019 | Litscher et al. |
| 10,478,325 B2 | | 11/2019 | Syed |
| 10,492,729 B2 | | 12/2019 | de la Rama et al. |
| 10,506,938 B2 | | 12/2019 | Wu et al. |
| 10,537,259 B2 | | 1/2020 | Wu et al. |
| 10,542,899 B2 | | 1/2020 | Wu et al. |
| 10,543,342 B2 | | 1/2020 | Obradovic |
| 10,556,091 B2 | | 2/2020 | Truhler et al. |
| 10,575,742 B2 | | 3/2020 | Wu et al. |
| 10,575,745 B2 | | 3/2020 | Solis |
| 10,595,738 B2 | | 3/2020 | Sterrett et al. |
| 10,595,740 B2 | | 3/2020 | Hoitink et al. |
| 10,602,948 B2 | | 3/2020 | Wu et al. |
| 10,646,692 B2 | | 5/2020 | Tegg et al. |

(56) References Cited

U.S. PATENT DOCUMENTS

| | | |
|---|---|---|
| 10,653,423 B2 | 5/2020 | Starnes |
| 10,702,677 B2 | 7/2020 | Okamura et al. |
| 10,737,060 B2 | 8/2020 | Gupta et al. |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,953,196 B2 | 3/2021 | Raab et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,141,568 B2 | 10/2021 | Hsueh et al. |
| 11,160,482 B2 | 11/2021 | Solis |
| D940,310 S | 1/2022 | de la Rama et al. |
| 11,272,886 B2 | 3/2022 | Harlev et al. |
| D951,438 S | 5/2022 | de la Rama et al. |
| D952,140 S | 5/2022 | de la Rama et al. |
| D952,843 S | 5/2022 | de la Rama et al. |
| 11,382,690 B2 | 7/2022 | Smith et al. |
| 11,382,743 B2 | 7/2022 | Marchand et al. |
| 11,383,078 B2 | 7/2022 | de la Rama et al. |
| 11,419,673 B2 | 8/2022 | Kauphusman et al. |
| 11,439,460 B2 | 9/2022 | Sliwa et al. |
| 11,446,471 B2 | 9/2022 | Grunewald |
| D966,506 S | 10/2022 | de la Rama et al. |
| D966,507 S | 10/2022 | de la Rama et al. |
| 11,471,216 B2 | 10/2022 | Harlev et al. |
| 11,478,299 B2 | 10/2022 | Webster et al. |
| 11,491,311 B2 | 11/2022 | Selkee |
| 11,511,078 B2 | 11/2022 | Gonzalez |
| 11,523,748 B2 | 12/2022 | Esguerra Wilczynski et al. |
| 11,540,876 B2 | 1/2023 | Oliverius et al. |
| 11,547,437 B2 | 1/2023 | Zarembinski |
| 11,583,334 B2 | 2/2023 | Caples et al. |
| 11,617,616 B2 | 4/2023 | Clark et al. |
| 11,617,859 B2 | 4/2023 | Hsueh et al. |
| 11,617,861 B2 | 4/2023 | Pai et al. |
| 11,622,806 B2 | 4/2023 | Romoscanu |
| 11,628,009 B2 | 4/2023 | Aujla |
| 11,660,119 B2 | 5/2023 | Hassett |
| 11,723,574 B2 | 8/2023 | Wu et al. |
| 11,793,567 B2 | 10/2023 | Harlev et al. |
| 11,806,152 B2 | 11/2023 | Zeidan et al. |
| 11,857,250 B2 | 1/2024 | Corvi et al. |
| 11,938,316 B2 | 3/2024 | Feler et al. |
| 11,950,897 B2 | 4/2024 | Esguerra Wilczynski et al. |
| 11,957,847 B2 | 4/2024 | Houck |
| 11,992,321 B2 | 5/2024 | Solis |
| 12,004,805 B2 | 6/2024 | Schuler et al. |
| 12,011,216 B2 | 6/2024 | Zirkle et al. |
| 12,036,371 B2 | 7/2024 | Hsueh et al. |
| 12,064,168 B2 | 8/2024 | Harlev et al. |
| 12,076,079 B2 | 9/2024 | Oliverius et al. |
| 12,089,940 B2 | 9/2024 | Hoitink et al. |
| 12,097,034 B2 | 9/2024 | Wu et al. |
| 12,109,031 B2 | 10/2024 | Deno et al. |
| 12,114,922 B2 | 10/2024 | Harlev et al. |
| 12,121,357 B2 | 10/2024 | de la Rama et al. |
| 12,121,438 B2 | 10/2024 | Dehdashtian et al. |
| 12,144,629 B2 | 11/2024 | Wu et al. |
| 12,193,823 B2 | 1/2025 | Wu et al. |
| 12,214,206 B2 | 2/2025 | Ward et al. |
| 12,232,908 B2 | 2/2025 | Stigall et al. |
| 12,246,143 B2 | 3/2025 | Leeflang et al. |
| 12,256,913 B2 | 3/2025 | Nunan |
| 12,256,984 B2 | 3/2025 | Ku et al. |
| 12,263,338 B2 | 4/2025 | de la Rama et al. |
| 12,324,620 B2 | 6/2025 | de la Rama et al. |
| 12,337,124 B2 | 6/2025 | Campbell et al. |
| 2002/0111585 A1 | 8/2002 | Lafontaine |
| 2002/0165484 A1 | 11/2002 | Bowe et al. |
| 2003/0032937 A1* | 2/2003 | Griego .............. A61M 25/0026 |
| | | 514/3.3 |
| 2003/0153942 A1 | 8/2003 | Wang et al. |
| 2004/0006305 A1 | 1/2004 | Hebert et al. |
| 2004/0109966 A1 | 6/2004 | Chen et al. |
| 2004/0122415 A1 | 6/2004 | Johnson |
| 2005/0065474 A1* | 3/2005 | Larson .............. A61M 25/0084 |
| | | 604/164.01 |
| 2006/0149165 A1 | 7/2006 | Kennedy et al. |
| 2007/0162101 A1 | 7/2007 | Burgermeister et al. |
| 2008/0154206 A1 | 6/2008 | Guo et al. |
| 2009/0312827 A1 | 12/2009 | Stapleton |
| 2012/0065612 A1 | 3/2012 | Stout et al. |
| 2013/0090608 A1 | 4/2013 | Stout et al. |
| 2013/0090610 A1 | 4/2013 | Stout et al. |
| 2014/0100639 A1 | 4/2014 | Lee et al. |
| 2015/0001191 A1 | 1/2015 | Lee et al. |
| 2015/0119911 A1 | 4/2015 | Mckenzie |
| 2015/0202421 A1 | 7/2015 | Ma et al. |
| 2015/0283357 A1 | 10/2015 | Lampropoulos et al. |
| 2016/0213423 A1 | 7/2016 | Kauphusman et al. |
| 2016/0278851 A1 | 9/2016 | Mannion et al. |
| 2016/0331933 A1 | 11/2016 | Knutsen |
| 2017/0319269 A1 | 11/2017 | Oliverius et al. |
| 2017/0367756 A1 | 12/2017 | Sliwa et al. |
| 2018/0042667 A1 | 2/2018 | Pappone et al. |
| 2018/0085064 A1 | 3/2018 | Auerbach et al. |
| 2018/0117279 A1 | 5/2018 | Yachia et al. |
| 2019/0192826 A1 | 6/2019 | Wada |
| 2020/0000359 A1 | 1/2020 | de la Rama et al. |
| 2020/0054391 A1 | 2/2020 | Litscher et al. |
| 2020/0138378 A1 | 5/2020 | de la Rama et al. |
| 2020/0253496 A1 | 8/2020 | Deno et al. |
| 2020/0405166 A1 | 12/2020 | Wu et al. |
| 2021/0145342 A1 | 5/2021 | Wang |
| 2021/0187246 A1 | 6/2021 | Houck |
| 2021/0204871 A1 | 7/2021 | Goedeke et al. |
| 2021/0267693 A1 | 9/2021 | Deno et al. |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0023594 A1 | 1/2022 | Pai |
| 2022/0054066 A1 | 2/2022 | Solis |
| 2022/0273913 A1 | 9/2022 | Worley et al. |
| 2022/0354568 A1 | 11/2022 | Pappone et al. |
| 2022/0370792 A1 | 11/2022 | de la Rama et al. |
| 2022/0387012 A1 | 12/2022 | Nunan |
| 2023/0011509 A1 | 1/2023 | Sterrett et al. |
| 2023/0084626 A1 | 3/2023 | Grunewald |
| 2023/0114222 A1 | 4/2023 | Esguerra Wilczynski et al. |
| 2023/0121397 A1 | 4/2023 | Oliverius et al. |
| 2023/0172661 A1 | 6/2023 | Harlev et al. |
| 2023/0190369 A1 | 6/2023 | Caples et al. |
| 2023/0329618 A1 | 10/2023 | Wu et al. |
| 2023/0329784 A1 | 10/2023 | Stewart et al. |
| 2024/0032997 A1 | 2/2024 | Harlev et al. |
| 2024/0081905 A1 | 3/2024 | Corvi et al. |
| 2024/0198054 A1 | 6/2024 | Schultz |
| 2024/0252815 A1 | 8/2024 | de la Rama et al. |
| 2024/0277277 A1 | 8/2024 | Hoitink et al. |
| 2024/0325691 A1 | 10/2024 | Bogusky |
| 2024/0415438 A1 | 12/2024 | Wu et al. |
| 2025/0009272 A1 | 1/2025 | Rama et al. |
| 2025/0025231 A1 | 1/2025 | Oliverius et al. |
| 2025/0032028 A1 | 1/2025 | Deno et al. |
| 2025/0032181 A1 | 1/2025 | Harlev et al. |
| 2025/0040853 A1 | 2/2025 | Wu et al. |
| 2025/0049460 A1 | 2/2025 | Worrell et al. |
| 2025/0082903 A1 | 3/2025 | Hsueh et al. |
| 2025/0090070 A1 | 3/2025 | Wu et al. |

(56) References Cited

U.S. PATENT DOCUMENTS

| | | | |
|---|---|---|---|
| 2025/0152932 | A1 | 5/2025 | de la Rama et al. |
| 2025/0160942 | A1 | 5/2025 | Ku et al. |

FOREIGN PATENT DOCUMENTS

| | | |
|---|---|---|
| CN | 106859765 A | 6/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 105960200 B | 8/2019 |
| CN | 105451680 B | 10/2019 |
| CN | 105960201 B | 3/2020 |
| CN | 111657866 A | 9/2020 |
| CN | 106264715 B | 11/2020 |
| CN | 106264716 B | 11/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |
| CN | 107773300 B | 8/2022 |
| CN | 106859638 B | 10/2022 |
| CN | 110547865 B | 10/2022 |
| CN | 107343816 B | 11/2022 |
| CN | 115444549 A | 12/2022 |
| CN | 107343784 B | 2/2023 |
| CN | 106419897 B | 6/2023 |
| CN | 112704546 B | 3/2024 |
| CN | 118384409 A | 7/2024 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2604306 B1 | 1/2014 |
| EP | 2752153 A1 | 7/2014 |
| EP | 2915555 A1 | 9/2015 |
| EP | 1968679 B1 | 9/2016 |
| EP | 2241279 B1 | 9/2016 |
| EP | 3115076 A4 | 10/2017 |
| EP | 3117863 A4 | 10/2017 |
| EP | 3030182 B1 | 1/2018 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3363397 A1 | 8/2018 |
| EP | 3391928 A1 | 10/2018 |
| EP | 3122276 B1 | 11/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3073908 B1 | 4/2019 |
| EP | 3466363 A1 | 4/2019 |
| EP | 2550989 B1 | 6/2019 |
| EP | 3512589 A1 | 7/2019 |
| EP | 3512590 A1 | 7/2019 |
| EP | 3527125 A1 | 8/2019 |
| EP | 3434218 B1 | 2/2020 |
| EP | 2908723 B1 | 3/2020 |
| EP | 3335658 B1 | 4/2020 |
| EP | 3073907 B1 | 6/2020 |

| | | |
|---|---|---|
| EP | 3114987 B1 | 8/2020 |
| EP | 3178516 B1 | 9/2020 |
| EP | 3708104 A1 | 9/2020 |
| EP | 3711662 A1 | 9/2020 |
| EP | 3721796 A1 | 10/2020 |
| EP | 3738508 A1 | 11/2020 |
| EP | 3738509 A1 | 11/2020 |
| EP | 3340916 B1 | 12/2020 |
| EP | 3750475 A1 | 12/2020 |
| EP | 2155301 B1 | 4/2021 |
| EP | 3432820 B1 | 4/2021 |
| EP | 2809254 B1 | 6/2021 |
| EP | 3508245 B1 | 7/2021 |
| EP | 3858277 A1 | 8/2021 |
| EP | 3791820 B9 | 4/2022 |
| EP | 3153124 B1 | 7/2022 |
| EP | 4039215 A1 | 8/2022 |
| EP | 4101372 A1 | 12/2022 |
| EP | 2844193 B1 | 1/2023 |
| EP | 3100696 B1 | 1/2023 |
| EP | 3166524 B1 | 1/2023 |
| EP | 4134032 A1 | 2/2023 |
| EP | 4179991 A1 | 5/2023 |
| EP | 2803329 B1 | 6/2023 |
| EP | 3015064 B1 | 6/2023 |
| EP | 3141183 B1 | 6/2023 |
| EP | 4190232 A1 | 6/2023 |
| EP | 2816966 B1 | 10/2023 |
| EP | 3113671 B1 | 10/2023 |
| EP | 3738509 B1 | 10/2023 |
| EP | 3209234 B1 | 11/2023 |
| EP | 3527125 B1 | 11/2023 |
| EP | 3721796 B1 | 11/2023 |
| EP | 4233699 A3 | 11/2023 |
| EP | 4272631 A2 | 11/2023 |
| EP | 3192442 B1 | 1/2024 |
| EP | 4298995 A2 | 1/2024 |
| EP | 3738508 B1 | 2/2024 |
| EP | 3124069 B1 | 4/2024 |
| EP | 4364765 A2 | 5/2024 |
| EP | 3498156 B1 | 6/2024 |
| EP | 4272631 A3 | 7/2024 |
| EP | 4205685 B1 | 8/2024 |
| EP | 4417112 A2 | 8/2024 |
| EP | 3184035 B1 | 10/2024 |
| EP | 4417112 A3 | 11/2024 |
| EP | 4101372 B1 | 12/2024 |
| EP | 2915555 B1 | 2/2025 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |
| JP | 6059737 B2 | 12/2016 |
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6479005 B2 | 2/2019 |
| JP | 6515084 B2 | 5/2019 |
| JP | 6528010 B1 | 6/2019 |
| JP | 6655655 B2 | 2/2020 |
| JP | 6746734 B2 | 8/2020 |
| JP | 6776021 B2 | 10/2020 |
| JP | 6776025 B2 | 10/2020 |

(56) References Cited

FOREIGN PATENT DOCUMENTS

| | | | |
|----|------------|----|---------|
| JP | 6786275 | B2 | 11/2020 |
| JP | 6821812 | B2 | 1/2021 |
| JP | 2021007772 | A | 1/2021 |
| JP | 6843502 | B2 | 3/2021 |
| JP | 6920312 | B2 | 8/2021 |
| JP | 6926306 | B2 | 8/2021 |
| JP | 6932484 | B2 | 8/2021 |
| JP | 6980386 | B2 | 12/2021 |
| JP | 2022020838 | A | 2/2022 |
| JP | 7101228 | B2 | 7/2022 |
| JP | 7102558 | B2 | 7/2022 |
| JP | 2023002720 | A | 1/2023 |
| JP | 7220242 | B2 | 2/2023 |
| JP | 7230168 | B2 | 2/2023 |
| JP | 7242816 | B2 | 3/2023 |
| JP | 7262919 | B2 | 4/2023 |
| JP | 7275333 | B2 | 5/2023 |
| JP | 7292822 | B2 | 6/2023 |
| JP | 7530317 | B2 | 8/2024 |
| JP | 2024103761 | A | 8/2024 |
| JP | 7628563 | B2 | 2/2025 |
| JP | 2025027101 | A | 2/2025 |
| JP | 7641330 | B2 | 3/2025 |
| WO | 9843530 | A1 | 10/1998 |
| WO | 0168178 | A1 | 9/2001 |
| WO | 2008091197 | A1 | 7/2008 |
| WO | 2017098198 | A1 | 6/2017 |
| WO | 2018053148 | A1 | 3/2018 |
| WO | 2018053164 | A1 | 3/2018 |

* cited by examiner

CATHETER INSERTION DEVICES

CROSS-REFERENCE TO RELATED APPLICATIONS

The present application is a Continuation of U.S. patent application Ser. No. 15/790,601 filed Oct. 23, 2017 (now U.S. Pat. No. 11,786,705); which claims the benefit of U.S. Provisional Appln No. 62/411,876 filed Oct. 24, 2016, the full disclosures which are incorporated herein by reference in their entirety for all purposes.

BACKGROUND OF THE INVENTION

The instant disclosure relates generally to catheter insertion devices.

Medical devices, such as introducer catheters, balloon catheters, dilatation catheters, and other similar devices can be used in a variety of diagnostic, therapeutic, and/or mapping and ablation procedures to diagnose and/or correct various cardiac conditions. Oftentimes, an introducer catheter or sheath can be used to guide a circular catheter, a balloon catheter, or other type of catheter into the body of a patient. The introducer catheter can include a hemostasis valve at its proximal end for preventing blood loss when the introducer is placed in a venous and/or arterial system. Since less blood is lost with a hemostasis valve, the need for blood transfusions may be reduced.

A catheter straightener may be used to facilitate insertion of a catheter into a hemostasis valve of an introducer catheter. Some catheter straighteners can comprise a solid, polymeric tube placed over a portion of the catheter, such that the catheter is housed in the catheter straightener. The distal end of the catheter straightener can be inserted into the proximal end of the hemostasis valve of the introducer catheter and the catheter can be distally advanced from the catheter straightener into the introducer catheter. The catheter straightener can aid in the alignment of the catheter and in some cases can help open the hemostasis valve to allow the catheter to be inserted into the introducer catheter and eventually into the body of the patient. In some embodiments, when the catheter straightener is inserted into the hemostasis valve, bleedback can occur; where blood from a venous and/or arterial system travels through the hemostasis valve into the catheter straightener. While some bleedback can be beneficial in confirming that the introducer catheter has accessed the venous and/or arterial system and that no air is introduced in the venous and/or arterial system, it is generally beneficial to limit the amount of bleedback to prevent excessive loss of blood from the patient.

BRIEF SUMMARY OF THE INVENTION

Various embodiments of the present disclosure provide a medical device straightener. The medical device straightener can comprise an elongate shaft extending along a shaft longitudinal axis, the elongate shaft including a shaft proximal end and a shaft distal end, wherein a shaft inner wall of the elongate shaft defines a shaft lumen extending therethrough. The medical device straightener can comprise a bleedback valve that includes an outer circumferential surface. The bleedback valve can be disposed at a distal end of the elongate shaft, within the shaft lumen, wherein a portion of the outer circumferential surface is in communication with the shaft inner wall. The bleedback valve can define a radially expandable lumen longitudinally extending through a center of the bleedback valve.

Various embodiments of the present disclosure can provide a catheter straightener. The catheter straightener can comprise an elongate shaft extending along a shaft longitudinal axis, the elongate shaft including a shaft proximal end and a shaft distal end, wherein a shaft inner wall of the elongate shaft defines a shaft lumen extending therethrough. The shaft inner wall can include a plurality of longitudinally extending ridges that extend along a portion of the shaft inner wall. A bleedback valve can be disposed at a distal end of the elongate shaft, within the shaft lumen, and can include an outer circumferential surface. A portion of the outer circumferential surface can be in communication with a distal portion of the shaft inner wall. The bleedback valve can define a radially expandable lumen longitudinally extending through a center of the bleedback valve and a plurality of bleedback ports that longitudinally extend along the circumferential surface of the bleedback valve.

Various embodiments of the present disclosure can provide a catheter insertion device. The catheter insertion device can include an elongate shaft that extends along a shaft longitudinal axis, the elongate shaft including a shaft proximal portion, a shaft middle portion, and a shaft distal portion, wherein the elongate shaft includes a shaft wall that defines a shaft lumen extending therethrough along the shaft longitudinal axis. A plurality of longitudinal features can extend through the shaft wall of the elongate shaft and can be configured to increase a rigidity of the elongate shaft. A bleedback valve can include an outer circumferential surface and can be disposed within the shaft lumen at a distal end of the shaft distal portion.

DETAILED DESCRIPTION

Figure 1:
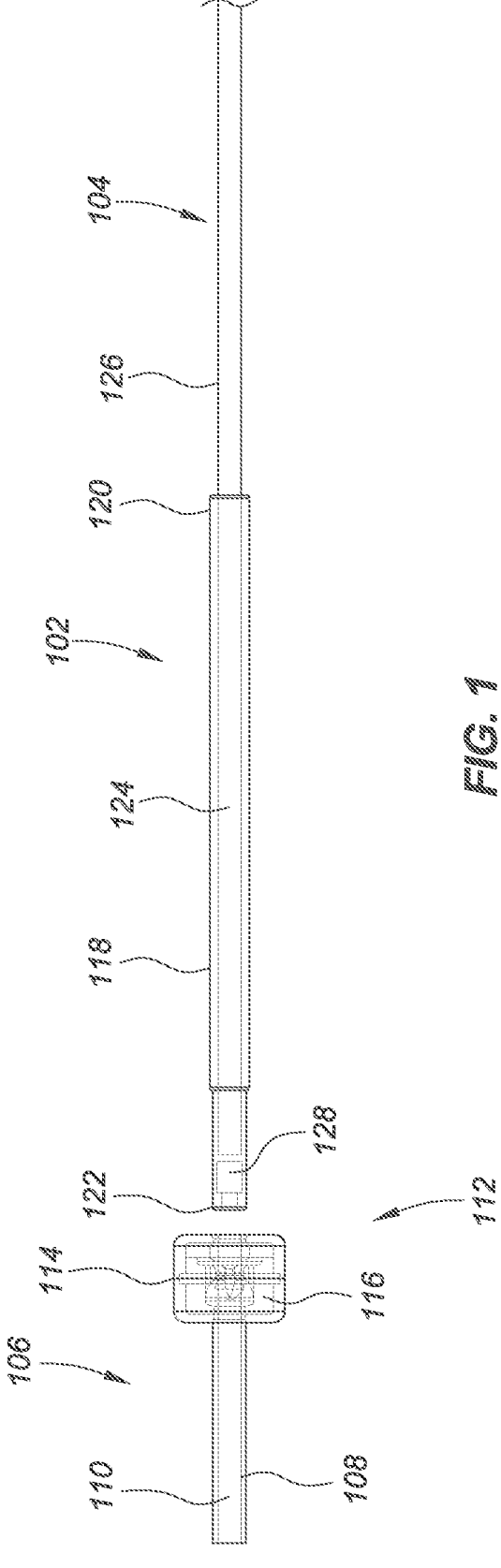
FIG. 1 is a partial cross-sectional view of a catheter insertion device in which a catheter has been inserted and an introducer catheter, in accordance with embodiments of the present disclosure.

FIG. 1 depicts a catheter insertion device 102 in which a catheter 104 has been inserted and an introducer catheter 106, in accordance with embodiments of the present disclosure. In some embodiments, the introducer catheter 106 can include an elongate introducer shaft 108 that extends along a longitudinal axis and defines an introducer lumen 110 that extends therethrough. A distal end of the introducer shaft 108 can be inserted into a venous and/or arterial system, providing access to the venous and/or arterial system via the introducer lumen 110. A proximal end of the introducer shaft 108 can be connected with a hemostasis valve 112, in some embodiments. The hemostasis valve 112 can include a casing 114 that surrounds an internal structure 116 of the hemostasis valve 112, further discussed herein. In some embodiments, the internal structure 116 of the hemostasis valve 112 can create a seal between the introducer lumen 110 and a proximal side of the hemostasis valve 112. As depicted, the internal structure 116 of the hemostasis valve 112 can be formed from a flexible material (e.g., silicon). When the distal end of the introducer shaft 108 is inserted into the venous and/or arterial system, the internal structure 116 can form a seal, preventing bodily fluid from passing through the introducer lumen 110 and out the proximal side of the hemostasis valve 112. Although the internal structure of the hemostasis valve 112 is discussed as being formed from a flexible material, the hemostasis valve can include other types of internal structures or types of seals, such as those discussed in relation to U.S. Pat. No. 8,905,973, which is hereby incorporated by referenced as though fully set forth herein.

In some embodiments, the hemostasis valve 112 can allow for a medical device (e.g., catheter) to be inserted through a proximal end of the hemostasis valve 112 and into the introducer lumen 110. The internal structure 116 of the hemostasis valve 112 can form a seal around the medical device, thus preventing bodily fluid from passing out of the proximal end of the hemostasis valve 112. In an example, the internal structure 116 of the hemostasis valve can deform to create an intimate seal around the medical device. In some embodiments, the medical device can include a catheter insertion device 102 (e.g., catheter straightener) and/or a catheter 104.

In some embodiments, a catheter 104 can have a flexible shaft and/or tip, which can make it difficult to insert the catheter 104 into the hemostasis valve 112. Although the internal structure 116 of the hemostasis valve 112 can generally be formed of a flexible material, initial introduction of the distal end of the catheter 104 into the hemostasis valve 112 can prove to be problematic. Accordingly, in some embodiments, a catheter insertion device 102 can be used to aid in delivery of the catheter 104 into the introducer lumen 110 and venous and/or arterial system. The catheter insertion device 102 can be beneficial to devices that have unique curved or formed distal designs, such as a circular mapping catheter, for instance. In an example, the catheter insertion device 102 can include an elongate shaft 118 that extends along a shaft longitudinal axis and comprises a shaft proximal end 120 and a shaft distal end 122. The elongate shaft 118 can be compatible with blood and other body fluids/tissue. In some embodiments, the elongate shaft 118 can comprise a biocompatible polymer material in accordance with embodiments of the present disclosure. For example, the elongate shaft 118 can comprise high density polyethylene (HDPE). The elongate shaft 118 can be flexible; however, the elongate shaft 118 can have sufficient rigidity to facilitate insertion of the elongate shaft 118 into the hemostasis valve 112.

In some embodiments, the elongate shaft 118 can define a shaft lumen 124 extending therethrough. The shaft lumen 124 can be defined by a shaft inner wall of the elongate shaft 118, as further discussed herein. The catheter 104 can include an elongate catheter shaft 126 that extends along the shaft longitudinal axis and can include a proximal end and a distal end. The elongate catheter shaft 126 can comprise a biocompatible polymer material and can include a flexibility that allows it to be threaded through a tortuous venous and/or arterial system. As previously discussed, this flexibility and/or design of the distal end of the catheter shaft 126 can make it difficult to insert the catheter shaft 126 through the hemostasis valve 112. In an example, some force can be required to penetrate the internal structure 116 of the hemostasis valve 112. However, the catheter shaft 126 may have a flexibility and/or a distal tip design that makes such penetration difficult.

Accordingly, the catheter shaft 126 can be disposed inside of the shaft lumen 124 of the catheter insertion device 102, which can generally be more rigid than the catheter shaft 126. The shaft distal end 122 of the catheter insertion device 102 can be inserted partially into or through the internal structure 116 of the hemostasis valve 112, allowing for the catheter 104 to be advanced into the introducer lumen 110.

However, as the catheter insertion device 102 is inserted into and/or through the hemostasis valve 112, the seal formed by the internal structure 116 can be penetrated and the introducer lumen 110 can be placed in fluid communication with the shaft lumen 124 of the elongate shaft 118. As a result, the shaft lumen 124 can be perfused with blood flowing from the venous and/or arterial system through the hemostasis valve 112 and into the shaft lumen 124, until the catheter 104 has been fully inserted through the hemostasis valve and the catheter insertion device 102 has been removed.

Some amount of blood perfusion into the shaft lumen 124 can be desirable. For example, blood perfusion into the shaft lumen 124 can provide an identifiable way for a physician to confirm that the venous and/or arterial system has been accessed. Additionally, blood perfusion into the shaft lumen 124 can ensure that no air is introduced into the venous and/or arterial system, by purging the introducer shaft 108 of air. However, it can be desirable to limit blood loss from the venous and/or arterial system due to perfusion into the shaft lumen 124, thus preventing the need for a blood transfusion to replace lost blood. Embodiments of the present disclosure can provide for a catheter insertion device 102 that can effectively limit an amount of blood loss from the venous and/or arterial system, while still providing for enough blood perfusion to ensure that the venous and/or arterial system is accessed and that no air is introduced into the venous and/or arterial system.

In some embodiments, the catheter insertion device 102 can include a bleedback valve 128 disposed in the distal end of the elongate shaft, within the shaft lumen 124. The bleedback valve 128 can create a seal and/or partial seal between the shaft lumen 124 and a distal exterior of the shaft distal end 122. As such, blood perfusion into the shaft lumen 124 can be reduced or eliminated altogether via the bleedback valve 128. The bleedback valve 128 can be configured to allow the catheter to pass through the bleedback valve 128, creating a seal around the elongate catheter shaft 126 of the catheter 104.

Figure 2:
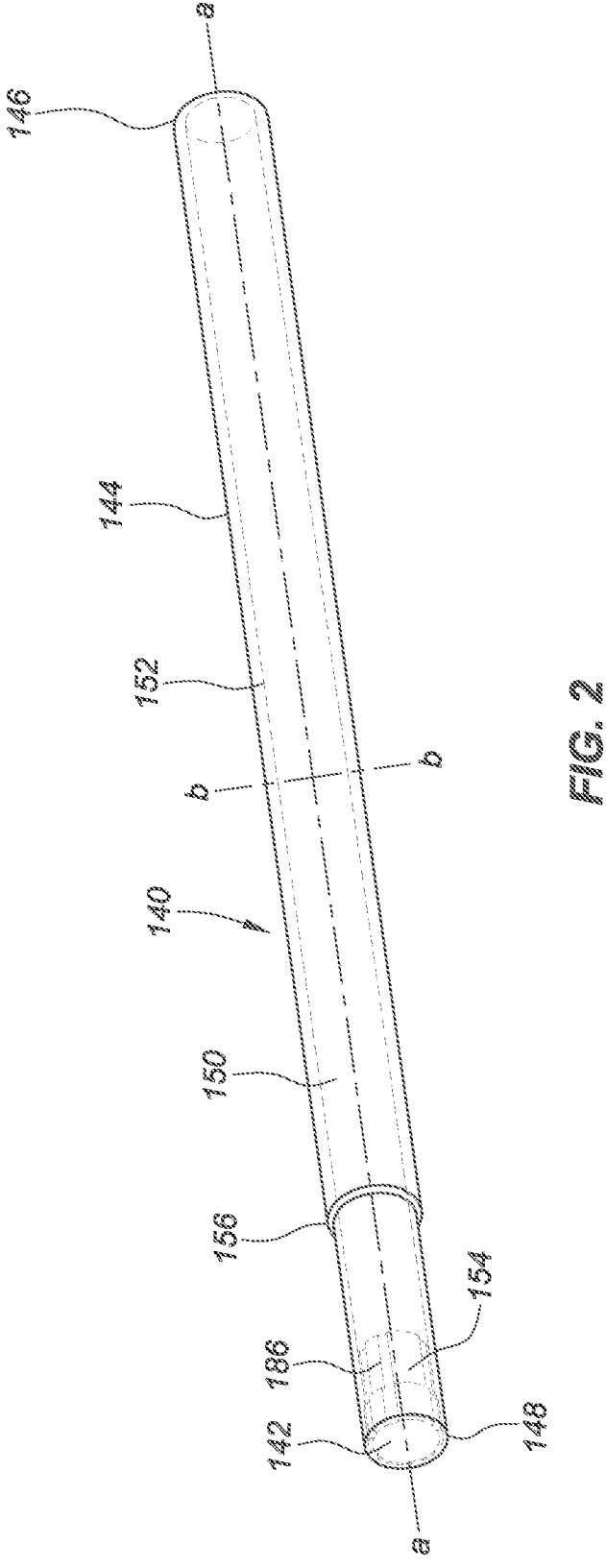
FIG. 2 is an isometric side, top, and distal end view of a catheter insertion device with a bleedback valve, in accordance with embodiments of the present disclosure.

FIG. 2 depicts an isometric side, top, and distal end view of a catheter insertion device 140 with a bleedback valve 142, in accordance with embodiments of the present disclosure. As previously discussed, the catheter insertion device 140 can include an elongate shaft 144 that extends along a shaft longitudinal axis aa and comprises a shaft proximal end 146 and a shaft distal end 148. In some embodiments, the elongate shaft 144 can have a uniform outside diameter. In some embodiments, as depicted, the elongate shaft 144 can have a varied outside diameter. For example, a shaft distal end 148 can have a diameter that is less than a diameter of a shaft middle portion of the elongate shaft, defined as an area between the shaft distal end 148 and the shaft proximal end 146. Alternatively, or in addition, the shaft proximal end can have an outer diameter that is less than an outer diameter of a shaft middle portion of the elongate shaft 144. In some embodiments, the comparatively smaller diameter shaft distal end 148 can allow for easier insertion of the elongate shaft 144 into a hemostasis valve. In some embodiments, a transition portion 156 can separate the shaft distal end 148 from the shaft middle portion. The transition portion 156 can be an area where the diameter of the shaft middle portion is gradually and/or abruptly transitioned into the diameter of the shaft distal end, thus facilitating insertion of the shaft distal end into the opening of the hemostasis valve. The elongate shaft 144 can be compatible with blood and other body fluids/tissue. The elongate shaft 144 can be flexible; however, the elongate shaft 144 can have sufficient rigidity, which also facilitates insertion of the elongate shaft 144 into the hemostasis valve. As previously discussed, the elongate shaft 144 can comprise a biocompatible polymer material in accordance with embodiments of the present disclosure.

In some embodiments, the elongate shaft 144 can define a shaft lumen 150 extending therethrough. The shaft lumen 150 can be defined by a shaft inner wall 152 (shown in phantom) of the elongate shaft 144, as further discussed herein. As discussed, the catheter insertion device 140 can include the bleedback valve 142, which can include an outer circumferential surface 154 disposed at a distal end of the elongate shaft 144, within the shaft lumen 150. In some embodiments, the bleedback valve 142 can be cylindrical in shape and can extend along the shaft longitudinal axis aa. For example, the bleedback valve 142 can be inserted into the shaft distal end 148 of the elongate shaft 144, making the elongate shaft 144 coaxial with the bleedback valve 142. A portion of the outer circumferential surface 154 can be in communication with the shaft inner wall 152. The outer circumferential surface 154 can be connected to the shaft inner wall 152 via an adhesive, press fitting, or other type of connection.

Figure 3A:
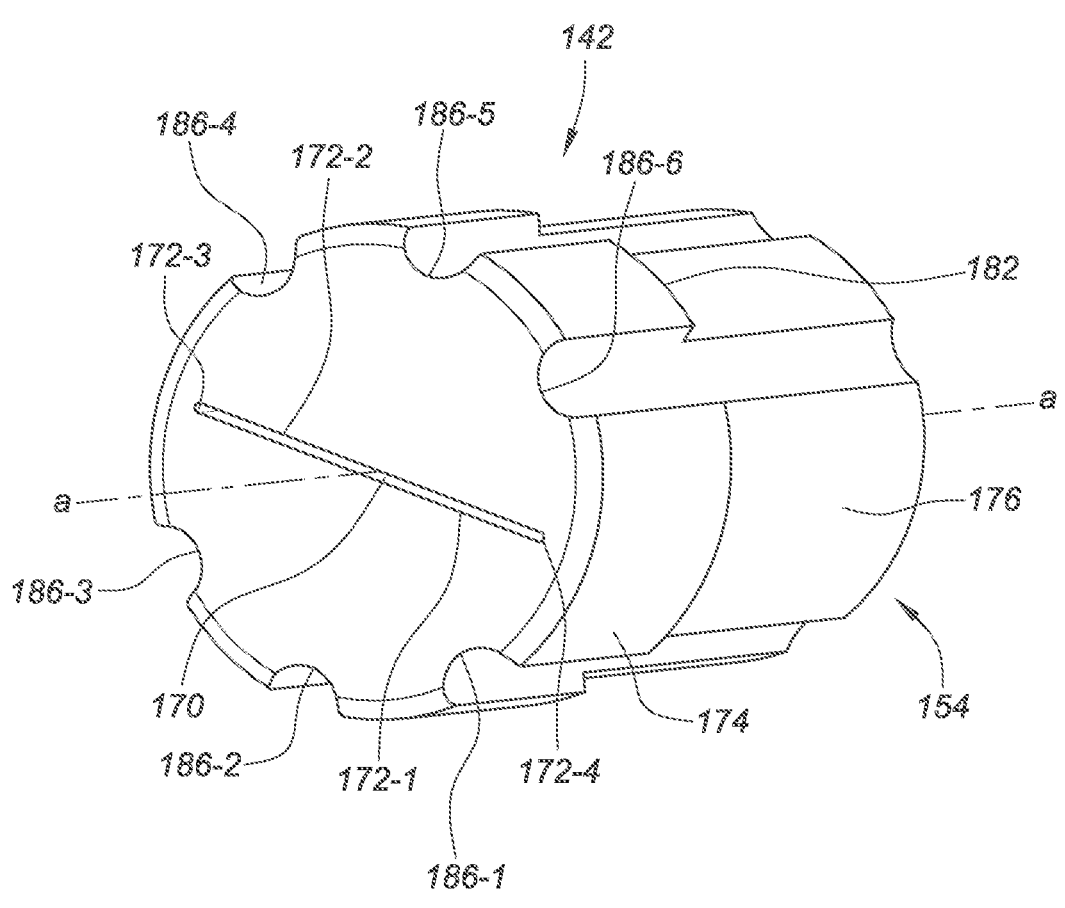
FIG. 3A is an enlarged isometric side, top, and distal end view of the bleedback valve depicted in FIG. 2, in accordance with embodiments of the present disclosure.

In some embodiments, the bleedback valve 142 can define a radially expandable lumen (further depicted in FIG. 3A) that longitudinally extends through a center of the bleedback valve 142, along the shaft longitudinal axis aa, which is further depicted and discussed herein, for example, in relation to FIG. 3A. A medical device (e.g., catheter) can be disposed within the shaft lumen 150 and advanced through the radially expandable lumen. In some embodiments, the bleedback valve 142 can be formed from an elastic material. For example, the bleedback valve 142 can comprise silicon rubber. When the catheter is in an undeployed state, the radially expandable lumen can remain closed. However, when the catheter is deployed from the shaft distal end 148, the radially expandable lumen can be stretched open via the catheter, while maintaining a seal around a shaft of the catheter.

FIG. 3A depicts an enlarged isometric side, top, and distal end view of the bleedback valve 142 depicted in FIG. 2, in accordance with embodiments of the present disclosure. In some embodiments, the bleedback valve 142 can include a radially expandable lumen 170. The radially expandable lumen 170 can extend along the shaft longitudinal axis aa, which can longitudinally extend through a center of the bleedback valve 142. In some embodiments, the radially expandable lumen 170 can be a slit extending through the center of the bleedback valve along the shaft longitudinal axis aa. The radially expandable lumen 170 can be defined by a bottom lumen wall 172-1, top lumen wall 172-2, and side lumen walls 172-3, 172-4, which all extend parallel with the shaft longitudinal axis aa. As the catheter is inserted through the radially expandable lumen 170, the bottom lumen wall 172-1 and the top lumen wall 172-2 can be spread apart, conforming to and creating a seal around the catheter shaft. In some embodiments, although the radially expandable lumen 170 is depicted as a slit, the radially expandable lumen 170 can be a hole that longitudinally extends through the bleedback valve 142. For example, the bleedback valve 142 can define a circular, square, triangular, oval, etc. shaped hole that extends through a center of the bleedback valve 142, along the shaft longitudinal axis aa.

In some embodiments, the bleedback valve 142 can include the circumferential surface 154. Although not depicted, the circumferential surface 154 of the bleedback valve 142 can have a uniform outside diameter, in some embodiments. Alternatively, the circumferential surface 154 can include a distal circumferential surface 174 (e.g., distal portion) of a first diameter and a proximal circumferential surface 176 (e.g., proximal portion) of a second diameter, wherein the first diameter is greater than the second diameter, thus creating a flared distal circumferential surface 176. Although not depicted, in some embodiments, the second diameter can be greater than the first diameter, creating a flared proximal circumferential surface. In some embodiments, the bleedback valve 142 can define a circumferential ledge 182 between the proximal circumferential surface 176 and the distal circumferential surface 174.

Figure 3B:
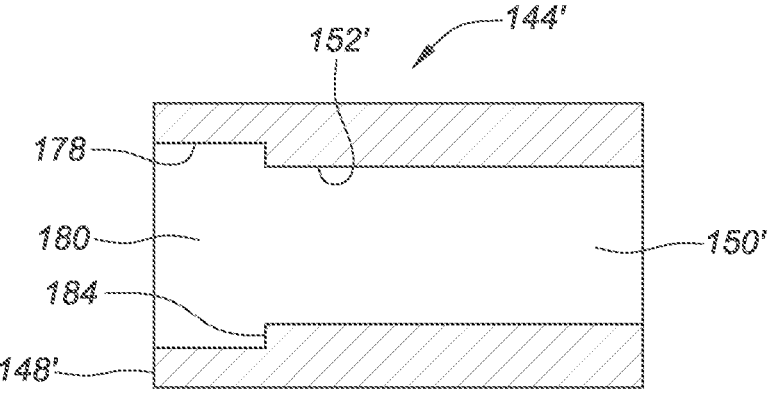
FIG. 3B is a cross-sectional view of a distal end of the catheter insertion device depicted in FIG. 2, in accordance with embodiments of the present disclosure.

In an example, the flared distal circumferential surface 174 can be beneficial when mounting the bleedback valve 142 in the distal end of the elongate shaft 144. In an example, as depicted in FIG. 3B, the elongate shaft 144' can include a shaft lumen 150' defined by a shaft inner wall 152, which can be of a first diameter. FIG. 3B is a cross-sectional view a distal end of a catheter insertion device in FIG. 2, in accordance with embodiments of the present disclosure. The shaft distal end 148' can include an expanded shaft lumen 180 defined by a distal shaft inner wall 178, which can be of a second diameter that is greater than the first diameter. In some embodiments, the bleedback valve 142 can be inserted into the shaft distal end 148' of the elongate shaft 144', such that the proximal circumferential surface 176 is disposed within the shaft lumen 150' and the flared distal circumferential surface 174 is disposed in the expanded shaft lumen 180. Accordingly, upon insertion of the bleedback valve 142 into the shaft distal end 148', the circumferential ledge can abut an inner shaft ledge 184, holding the bleedback valve 142 in place.

With further reference to FIG. 3A, the bleedback valve 142 can define a plurality of bleedback grooves 186-1, 186-2, 186-3, 186-3, 186-4, 186-5, 186-6 that longitudinally extend along the circumferential surface 154 of the bleedback valve 142. Hereinafter, bleedback grooves are referred to in the plural as bleedback grooves 186. The plurality of bleedback grooves 186 can extend parallel with the shaft longitudinal axis aa, in some embodiments. In some embodiments, the bleedback grooves 186 can be defined in the circumferential surface 154, such that the bleedback grooves 186 are divergent with the shaft longitudinal axis aa (e.g., are disposed at an angle with respect to the shaft longitudinal axis aa). In some embodiments, the bleedback grooves 186 can helically encircle the bleedback valve 142. The bleedback grooves 186 can be semicircular grooves that extend along the circumferential surface 154. In some embodiments, the bleedback grooves 186 can be square, triangular, etc. in shape.

Figure 3C:
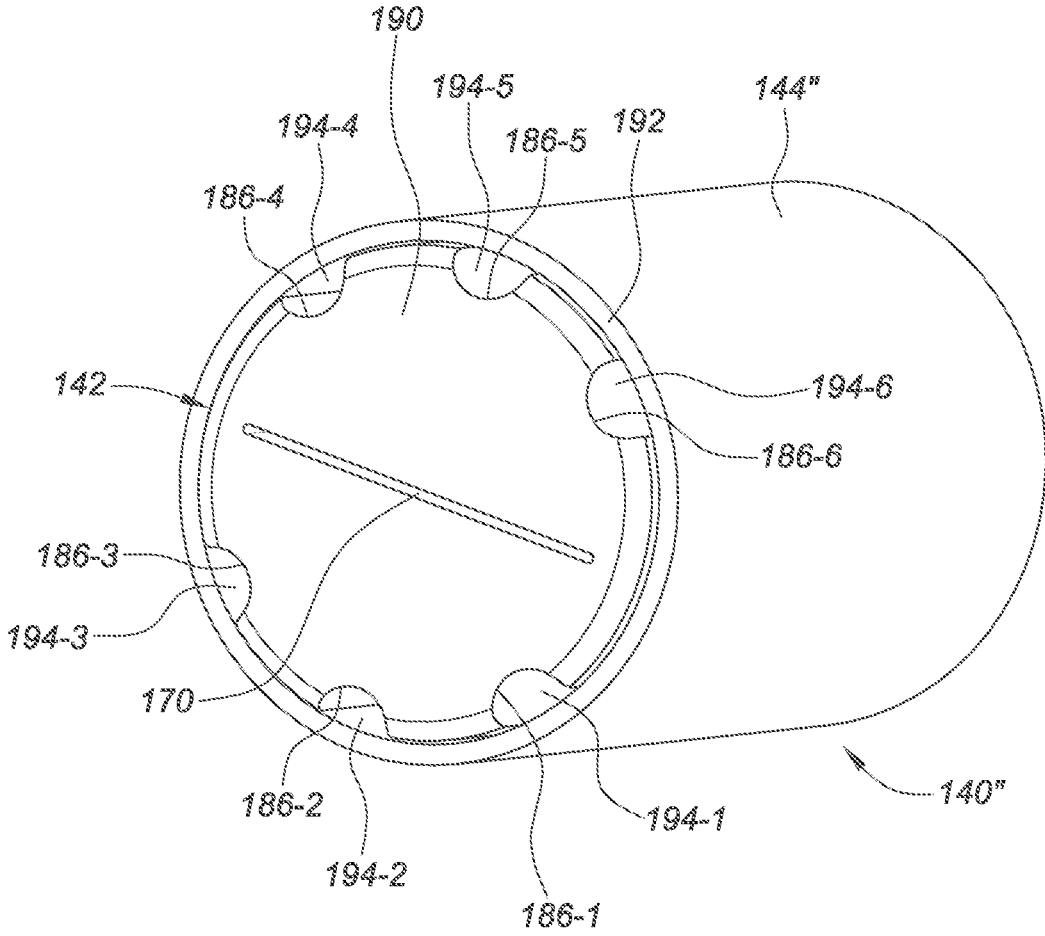
FIG. 3C is an enlarged isometric side, top, and distal end view of a distal end of the catheter insertion device with a bleedback valve depicted in FIG. 2, in accordance with embodiments of the present disclosure.

FIG. 3C is an enlarged isometric side, top, and distal end view of a distal end of the catheter insertion device 140" with the bleedback valve 142 depicted in FIG. 3A, in accordance with embodiments of the present disclosure. In some embodiments, as discussed herein, the portion of the outer circumferential surface of the bleedback valve 142 can be connected to the shaft inner wall of the elongate shaft 144". The bleedback valve 142 can be inserted into the elongate shaft 144", such that a distal valve face 190 of the bleedback valve 142 is located in a same longitudinal position as a distal shaft face 192 of the elongate shaft 144". However, in some embodiments, the bleedback valve 142 can be inserted into the elongate shaft 144", such that the distal valve face 190 of the bleedback valve 142 is located proximally with respect to the distal shaft face 192 of the elongate shaft 144". In some embodiments, the bleedback valve 142 can be inserted into the elongate shaft 144", such that the distal valve face 190 of the bleedback valve 142 is located distally with respect to the distal shaft face 192 of the elongate shaft 144".

In some embodiments where the bleedback valve 142 is connected to the shaft inner wall of the elongate shaft 144", the bleedback grooves 186 and an opposing portion of the shaft inner wall with respect to each bleedback groove 186 can form a plurality of bleedback ports 194-1, 194-2, 194-3, 194-5, 194-6, hereinafter referred to in the plural as bleedback ports 194. The bleedback ports 194 can be semi cylindrical in shape. The bleedback ports 194 can allow blood to perfuse from a distal exterior of the catheter insertion device 140", through the bleedback ports 194 and into a shaft lumen 150 (FIG. 2) of the catheter insertion device 140". As previously discussed, some amount of blood perfusion into the shaft lumen 150 can be desirable. For example, blood perfusion into the shaft lumen 150 can provide an identifiable way for a physician to confirm that the venous and/or arterial system has been accessed. Additionally, blood perfusion into the shaft lumen 150 can ensure that no air is introduced into the venous and/or arterial system by purging the introducer shaft 108 (FIG. 1) of air. However, it can be desirable to limit blood loss from the venous and/or arterial system due to perfusion into the shaft lumen 150, thus preventing the need for a blood transfusion to replace lost blood.

Although six bleedback grooves 186 and six bleedback ports 194 are depicted, embodiments of the present disclosure can include greater than or fewer than six bleedback grooves 186 and/or six bleedback ports 194. In an example, embodiments of the present disclosure can include from 1 to 20 bleedback grooves 186 and/or bleedback ports 194. In some embodiments, the bleedback valve 142 can be formed from a solid piece of elastic material with the radially expandable lumen 170 extending therethrough. In some embodiments, the bleedback valve 142 can include a hollow cylindrical body that includes a distal valve face 190 disposed at a distal end of the hollow cylindrical body, through which the radially expandable lumen 170 can extend.

Figure 4A:
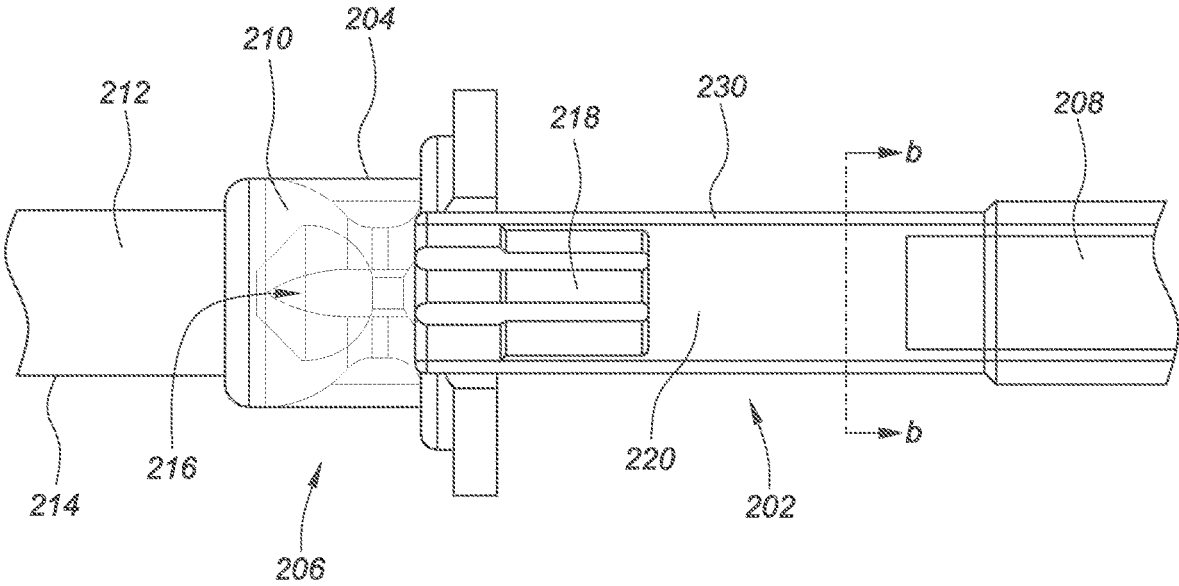
FIG. 4A is a schematic view of a catheter insertion device partially inserted into a hemostasis valve of an introducer catheter and a catheter positioned within the catheter insertion device, in accordance with embodiments of the present disclosure.
Figure 4B:
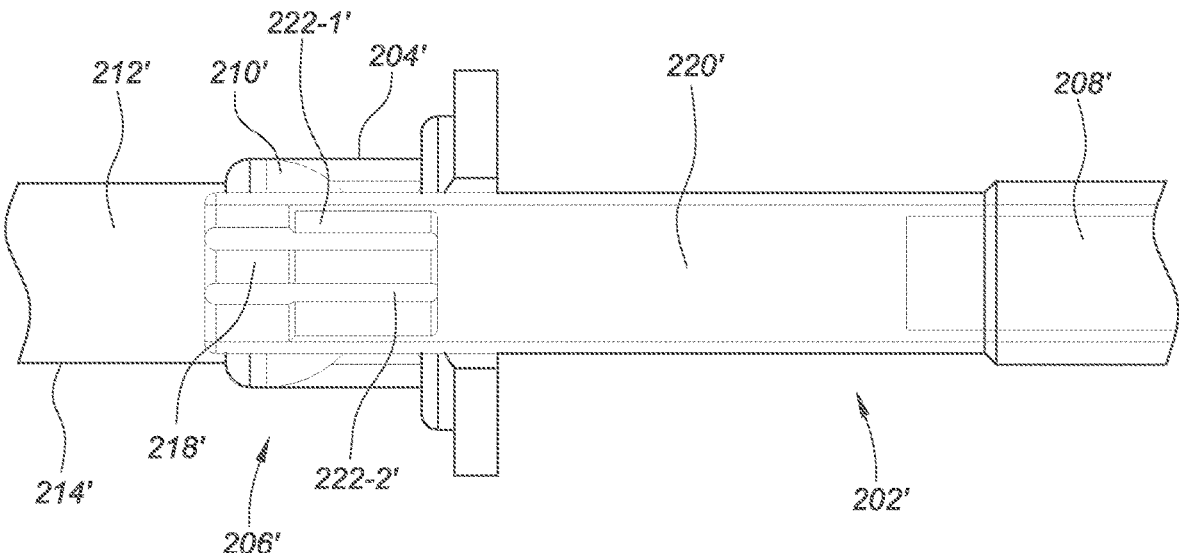
FIG. 4B is a schematic view of the catheter insertion device depicted in FIG. 4A fully inserted into the hemostasis valve of the introducer catheter and the catheter positioned within the catheter insertion device, in accordance with embodiments of the present disclosure.

FIG. 4A is a schematic view of a catheter insertion device 202 partially inserted into a hemostasis valve 204 of an introducer catheter 206 and a catheter 208 positioned within the catheter insertion device 202, in accordance with embodiments of the present disclosure. As previously discussed in relation to FIG. 1, the hemostasis valve 206 can include an internal structure 210 that can form a seal, preventing bodily fluid from passing through an introducer lumen 212 of an introducer shaft 214 coupled to the distal side of the hemostasis valve 204 and out the proximal side of the hemostasis valve 204. In an example, the internal structure 210 can define a radially expandable lumen 216 that can be radially expanded upon insertion of a medical device (e.g., catheter insertion device 202 and/or catheter 208) through the radially expandable lumen 216. As depicted, a distal tip of the catheter insertion device 202 has been partially inserted into a proximal end of the hemostasis valve 204, such that a distal face of a bleedback valve 218 disposed in the distal end of the catheter insertion device 202 is disposed within the radially expandable lumen 216 of the hemostasis valve. As depicted in FIG. 4B, the distal tip of the catheter insertion device 202 can be inserted through the hemostasis valve 204, such that the distal tip of the catheter insertion device is located in the introducer lumen 212.

FIG. 4B is a schematic view of a catheter insertion device 202' fully inserted into a hemostasis valve 204' of an introducer catheter 206' and a catheter 208' positioned within the catheter insertion device 202', in accordance with embodiments of the present disclosure. As depicted, the distal end of the catheter insertion device 202' has been inserted all the way through the hemostasis valve 204', causing a distal face of the bleedback valve 218' to be in fluid communication with the introducer lumen. Embodiments of the present disclosure can prevent and/or limit perfusion of blood, air, and/or bodily fluid from the introducer lumen 212' into a shaft lumen 220' of the catheter insertion device 202'. For example, as depicted in FIG. 4B, the bleedback valve 218' includes a plurality of bleedback grooves 222-1', 222-2' that can allow for fluid to travel from the introducer lumen 212' through the bleedback grooves 222-1', 222-2' and into the shaft lumen 220'. However, in some embodiments that are not shown, the bleedback valve 218' may not include bleedback grooves, thus creating a fluid tight seal between an outer circumferential surface of the bleedback valve and an inner wall of the catheter insertion device 202' that defines the shaft lumen 220'.

Figure 4C:
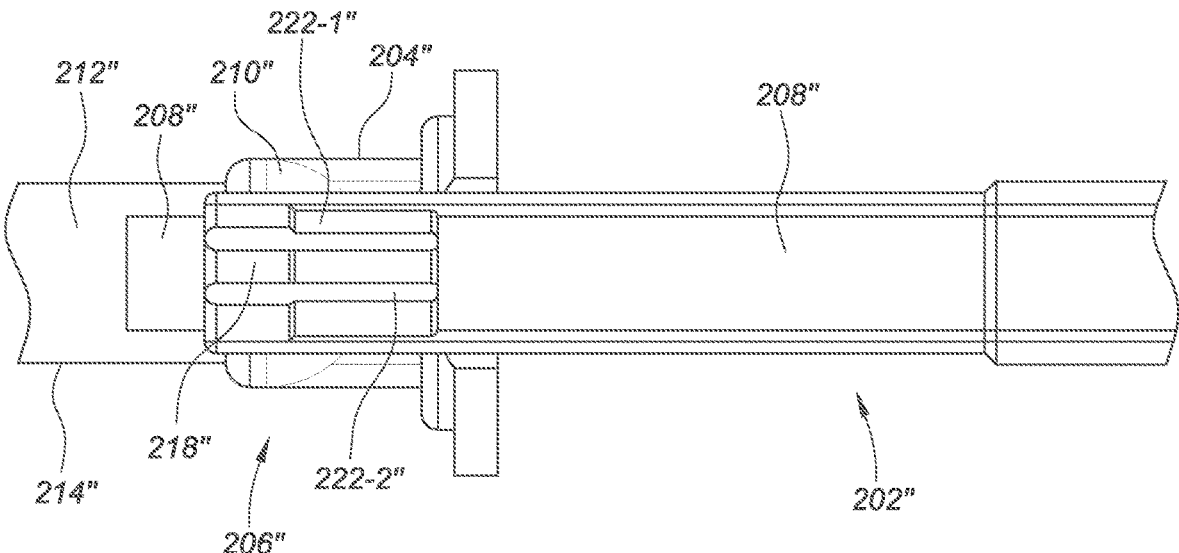
FIG. 4C is a schematic view of the catheter insertion device depicted in FIG. 4A fully inserted into the hemostasis valve of the introducer catheter and the catheter inserted through the bleedback valve of the catheter insertion device, in accordance with embodiments of the present disclosure.

FIG. 4C is a schematic view of a catheter insertion device 202" fully inserted into a hemostasis valve 204" of an introducer catheter 206" and a catheter 208" inserted through a bleedback valve 218" of catheter insertion device 202", in accordance with embodiments of the present disclosure. The catheter 208" can be advanced through the bleedback valve 218" via insertion of the distal end of the catheter 208" through the radially expandable lumen of the bleedback valve 218". Upon insertion of the distal end of the catheter 208" into the radially expandable lumen, the lumen can expand to a size that is approximately equal to an outside diameter of the catheter 208", thus forming a seal between the bleedback valve 218" and the catheter 208". The catheter 208" can be further advanced through the bleedback valve 218", the hemostasis valve 204", and the introducer lumen 212" into a venous and/or arterial system.

Figure 4D:
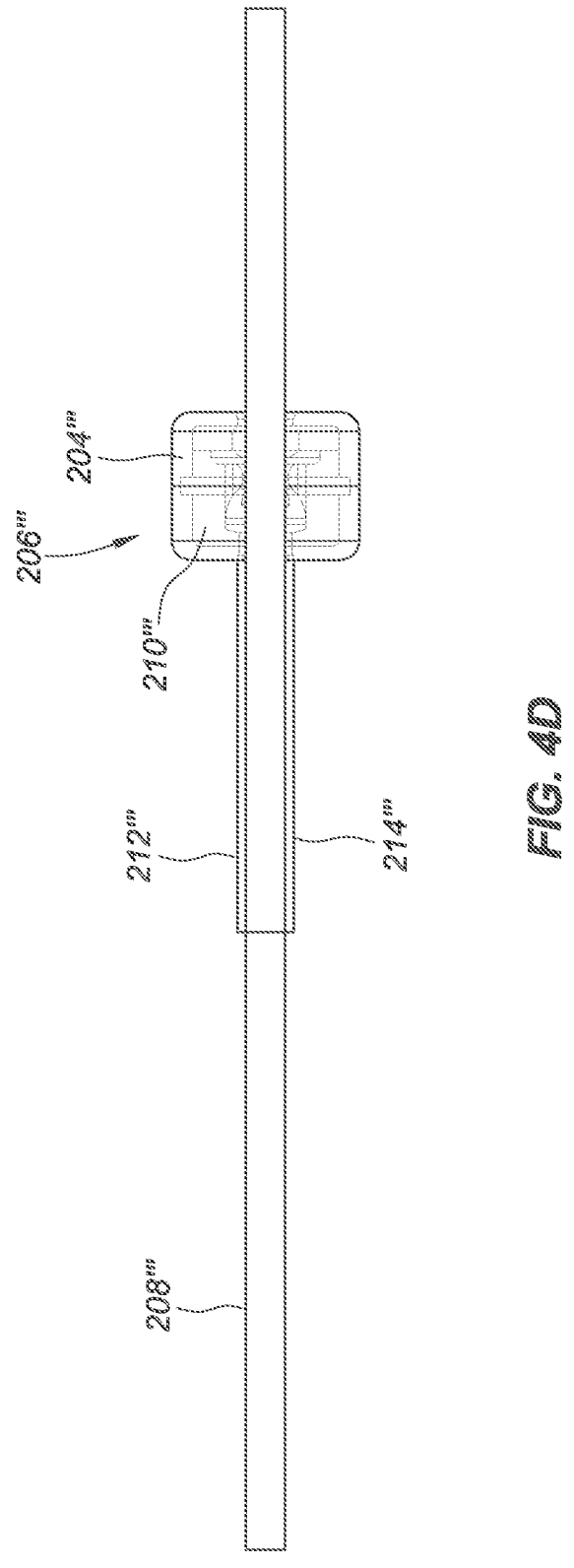
FIG. 4D is a schematic view of the catheter depicted in FIG. 4A fully inserted through the hemostasis valve and through an introducer shaft of the introducer catheter, in accordance with embodiments of the present disclosure.

FIG. 4D is a schematic view of the catheter 208'" depicted in FIG. 4A fully inserted through the hemostasis valve 204'" and through the introducer shaft 214'" of the introducer catheter 206'", in accordance with embodiments of the present disclosure. As depicted, the catheter 208'" has been fully advanced through the hemostasis valve 204'" and through the introducer lumen 212'" out of the distal end of the introducer shaft 214'". As further depicted in FIG. 4D, the catheter insertion device 202" has been removed.

With further reference to FIG. 4C, in some embodiments, the catheter insertion device 202" can be removed by peeling the catheter insertion device 202" away from the shaft of the catheter 208". For example, the catheter insertion device 202" may not be slid off of the shaft of the catheter 208" because the hemostasis valve 204" and the patient are located distally with respect to the catheter insertion device 202" and a catheter control handle is located proximally with respect to the catheter insertion device 202". The catheter insertion device 202" can be split in half along a longitudinal axis of the catheter insertion device 202".

Figure 5A:
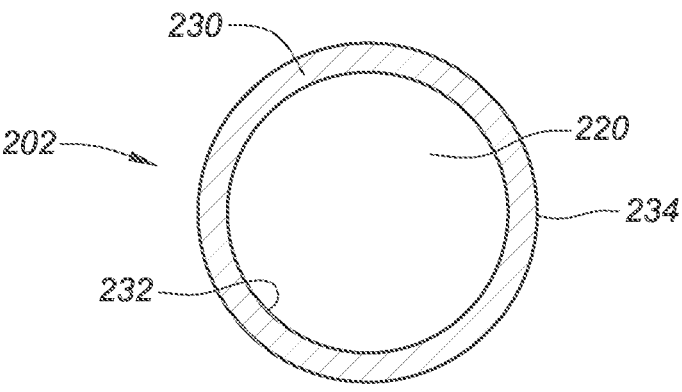
FIG. 5A is a cross-sectional end view of the catheter insertion device depicted in FIG. 4A, along the line bb, in accordance with embodiments of the present disclosure.

FIG. 5A is a cross-sectional view of the catheter insertion device 202 depicted in FIG. 4A, along the line bb, in accordance with embodiments of the present disclosure. The catheter insertion device 202 can be an elongate shaft formed by a longitudinally extending circumferential shaft wall 230 that includes a shaft inner wall 232 and a shaft outer wall 234. In some embodiments, the shaft wall 230 can be formed from a biocompatible polymer material that has a sufficient rigidity to facilitate insertion of the elongate shaft into a hemostasis valve. In some embodiments, the material forming the shaft wall 230 can be transparent and/or translucent to visually confirm access to the venous and/or arterial system. In an example, blood can perfuse through the bleedback valve upon accessing the venous and/or arterial system and can enter the shaft lumen 220 of the elongate shaft 202, which can serve as a visible confirmation that the venous and/or arterial system has been accessed. For instance, a physician can visually confirm that blood has perfused into the shaft lumen 220 through the bleedback valve due to the translucency and/or transparency of the shaft wall 230.

Figure 5B:
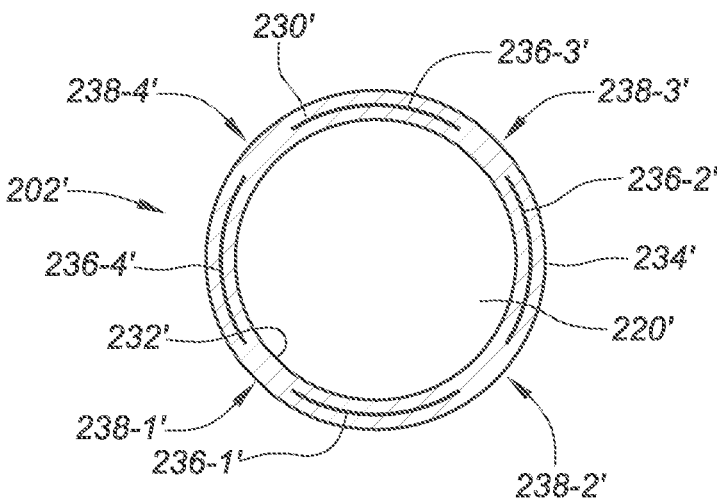
FIG. 5B is a cross-sectional end view of the catheter insertion device depicted in FIG. 4A, along the line bb, that includes four longitudinal features, in accordance with embodiments of the present disclosure.

FIG. 5B is a cross-sectional view of the catheter insertion device 202' depicted in FIG. 4A, along the line bb, that includes a plurality of longitudinal features 236-1', 236-2', 236-3', 236-4', in accordance with embodiments of the present disclosure. Hereinafter, the longitudinal features 236-1', 236-2', 236-3', 236-4' are referred to herein as longitudinal features 236'. In some embodiments, the longitudinal features 236' can longitudinally extend along a portion of the length of the catheter insertion device 202'. In an example, the longitudinal features 236' can extend from a distal end of the catheter insertion device 202' to a point along the catheter insertion device 202' located distally with respect to the proximal end. In some embodiments, the longitudinal features 236' can extend from a proximal end of the catheter insertion device 202' to a point along the catheter insertion device 202' located proximally with respect to the distal end. In some embodiments, the longitudinal features 236' can extend along an entire length of the catheter insertion device 202'.

The longitudinal features 236' can be circumferentially spaced about the shaft wall 230'. In some embodiments, the longitudinal features 236' can be equally spaced about the shaft wall 230', as depicted. A first longitudinal feature 236-1' can be diametrically opposed with respect to a third longitudinal feature 236-3' and a second longitudinal feature 236-2' can be diametrically opposed with respect to a fourth longitudinal feature 236-4'.

Although the longitudinal features 236' are depicted as partial circumferentially extending cross-sections that extend around a portion of the circumference of the shaft wall, the longitudinal features 236' can be formed of a material with a circular, square, triangular, rectangular, etc. cross-section. The longitudinal features 236' can be formed from a material (e.g., polymer) that has an increased durometer versus the material that forms the shaft wall 230'. The longitudinal features 236' can increase an overall stiffness and/or pushability of the catheter insertion device 202', while maintaining windows of translucent and/or transparent material that forms the shaft wall 230' between the longitudinal features 236'. In an example, some material that forms the longitudinal features 236' can be opaque and/or semi-opaque, which may not enable a user to see through the longitudinal features 236'. Accordingly, windows can be located at areas 238-1', 238-2', 238-3', 238-4' between the longitudinal features 236' to enable a physician to see into the shaft lumen 220'.

In some embodiments, the longitudinal features 236' can maintain a peelability of the catheter insertion device 202'. For example, as previously discussed, the catheter insertion device 202' can be peeled away from a catheter that extends through the catheter insertion device 202'. The areas 238-1', 238-2', 238-3', 238-4' located between the longitudinal features 236' can be weakened in relation to the areas of the shaft wall 230' that include the longitudinal features 236'. Accordingly, a physician can pull on a distal or proximal end of one or more of the longitudinal features 236', separating the particular longitudinal feature(s) 236' being pulled on and the portion of the shaft wall 230' containing the particular longitudinal feature(s) 236'. For example, portions of the shaft wall 230' located at the areas 238-1', 238-2', 238-3', and/or 238-4' can be torn as a result of the physician pulling the distal or proximal end of one or more of the longitudinal features 236'.

In some embodiments, the longitudinal features 236' can be coextruded with the shaft wall 230'. Although the longitudinal features 236' are depicted as being disposed between the shaft inner wall 232' and the shaft outer wall 234', the longitudinal features 236' can be disposed in the shaft wall 230' such that they are flush with the shaft inner wall 232' and/or the shaft outer wall 234'.

Figure 5C:
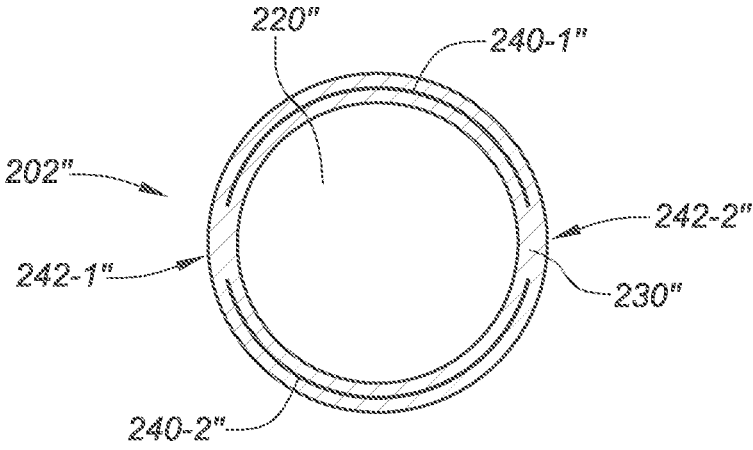
FIG. 5C is a cross-sectional end view of the catheter insertion device depicted in FIG. 4A, along the line bb, that includes two longitudinal features, in accordance with embodiments of the present disclosure.

Although four longitudinal features 236' are depicted as being disposed in the shaft wall 230', fewer than or greater than four longitudinal features 236' can be disposed in the shaft wall 230'. For example, as depicted in FIG. 5C, two longitudinal features 240-1", 240-2" can be disposed in the shaft wall 230". FIG. 5C is a cross-sectional view of the catheter insertion device 202" depicted in FIG. 4A, along the line bb, that includes a plurality of longitudinal features 240-1", 240-2", in accordance with embodiments of the present disclosure. The catheter insertion device 202" can include features similar to or the same as those discussed in relation to the catheter insertion device 202" depicted in FIG. 5B, with the exception that two longitudinal features 240-1", 240-2" are included in the catheter insertion device 202".

As previously discussed in relation to FIG. 5B, windows can be located at areas 242-1", 242-2" between the longitudinal features 240-1", 240-2" to enable a physician to see into the shaft lumen 220". The longitudinal features 240-1", 240-2" can maintain a peelability of the catheter insertion device 202". For example, as previously discussed, the catheter insertion device 202" can be peeled away from a catheter that extends through the catheter insertion device 202". The areas 242-1", 242-2" located between the longitudinal features 240-1", 240-2" can be weakened in relation to the areas of the shaft wall 230" that includes the longitudinal features 240-1", 240-2", as previously discussed in relation to FIG. 5B.

Figure 6A:
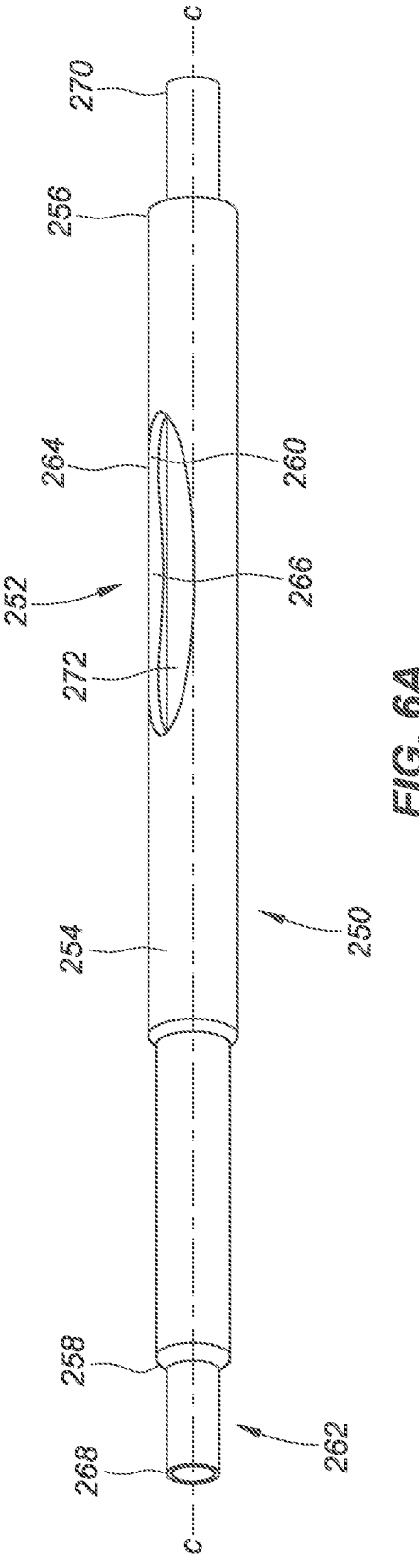
FIG. 6A is an isometric, side, top, and distal end view of a catheter insertion device that includes an access lumen, in accordance with embodiments of the present disclosure.

FIG. 6A is an isometric, side, top, and distal end view of a catheter insertion device 250 that includes an access lumen 252, in accordance with embodiments of the present disclosure. The catheter insertion device 250 can comprise an elongate shaft 254 that extends along a shaft longitudinal axis cc and comprises a shaft proximal end 256 and a shaft distal end 258. A shaft inner wall 260 of the elongate shaft can define a shaft lumen extending therethrough. FIG. 6A further depicts a catheter 262 that is disposed within the shaft lumen of the catheter insertion device 250. In some embodiments, the access lumen 252 can extend between the shaft inner wall 256 and a shaft outer wall 264 and can be defined by a lumen wall 266. As depicted, the access lumen 252 can be axially elongated. Although the access lumen 252 is depicted as oval in shape, the access lumen 252 can be circular, rectangular, square, triangular, etc.

As depicted, the catheter 262 can include a catheter distal end 268 and a catheter proximal end 270, as well as a middle portion 272. The catheter 262 is depicted as having been advanced through the catheter insertion device 250, such that the catheter distal end 268 is located distally with respect to the shaft distal end 258. The access lumen 252 allows access to a particular portion of the catheter 262 depending on how far the catheter 262 has been advanced through the catheter insertion device 250. For example, access is provided to the middle portion 272 via the access lumen 252. In some embodiments, a physician can grasp the catheter insertion device 250 with their hand to advance the shaft distal end 258 of the catheter insertion device 250 into and/or through a hemostasis valve associated with a catheter introducer. Upon insertion of the catheter insertion device 250 into the catheter introducer, the catheter 262 can be distally advanced (e.g., protracted) from the catheter insertion device 250. In some embodiments, a degree at which the catheter 262 is advanced can be controlled via a physician placing a finger on a portion of the catheter 262 (e.g., middle portion 272) via the access hole. Friction can exist between the catheter 262 and the physician's finger (e.g., gloved finger), controlling the longitudinal movement of the catheter 262. Some catheters have a natural bend and can have a propensity to return to their natural state when straightened inside the catheter insertion device 250, causing the catheter to move longitudinally either proximally or distally with respect to the catheter insertion device 250. This movement can be controlled via the access lumen 252.

Figure 6B:
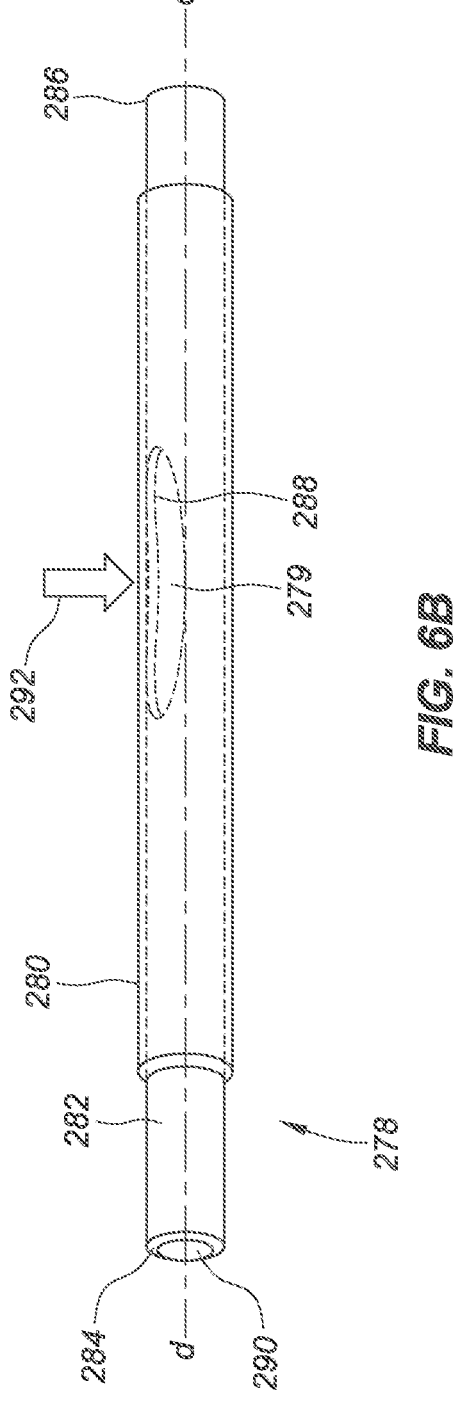
FIG. 6B is an isometric, side, top, and distal end view of a catheter insertion device that includes an access lumen covered with an elastic material, in accordance with embodiments of the present disclosure.

FIG. 6B is an isometric, side, top, and distal end view of a catheter insertion device 278 that includes an access lumen 279 covered with an elastic material 280, in accordance with embodiments of the present disclosure. The catheter insertion device 278 can comprise an elongate shaft 282 that extends along a shaft longitudinal axis dd and further comprises a shaft proximal end 284 and a shaft distal end 286. A shaft inner wall 288 of the elongate shaft 282 can define a shaft lumen 290 extending therethrough. In some embodiments, the elastic material 280 can be concentric with the elongate shaft 282 and can extend distally and proximally with respect to the access lumen 279. The elastic material can be formed from a rubber in some embodiments, such as latex, silicon, etc.

In some embodiments an inner diameter of the elastic material 280 in its natural state can be less than an outer diameter of the elongate shaft 282. Accordingly, the elastic material 280 can be stretched over the elongate shaft 282, forming a fluid tight seal between the shaft lumen 290 and an exterior of the elastic material 280. In some embodiments, the elastic material 280 can be connected with the elongate shaft 282 (e.g., via an adhesive). In contrast to FIG. 6A, the shaft lumen 290 is not open to an area exterior to the elastic material 280. This can prevent blood that has perfused into the shaft lumen 290 from exiting the access lumen 279.

However, a physician is still able to grasp the catheter insertion device 278 and depress on the elastic material 280 covering the access lumen 279 in a direction of arrow 292. This can cause an interior surface of the elastic material 280 to come into contact with a catheter shaft (not depicted) disposed within the shaft lumen 290, creating friction between an exterior surface of the catheter shaft and the interior surface of the elastic material 280 covering the access lumen 279. This can allow for control of longitudinal movement of the catheter.

Although the elastic material 280 is depicted as a tube that extends proximally and distally with respect to the access lumen 279, in some embodiments the elastic material can be a sheet of elastic material that is connected to an outer surface of the catheter insertion device 278, such that it covers the access lumen 279. In an example, the elastic material can be adhered to the outer surface of the catheter insertion device 278. For instance, the elastic material can be adhered around a perimeter of the access lumen 279.

In some embodiments, the access lumen 279 can be formed in the catheter insertion device 278 by cutting or machining the catheter insertion device 278 to create the access lumen 279. However, in some embodiments, one or more core pins can be added to an injection mold for the catheter insertion device 278 that are in the shape of the access lumen 279. As such, the injection mold for the catheter insertion device 278 can be modified and not replaced with a new injection mold, which can save resources.

Figure 6C:
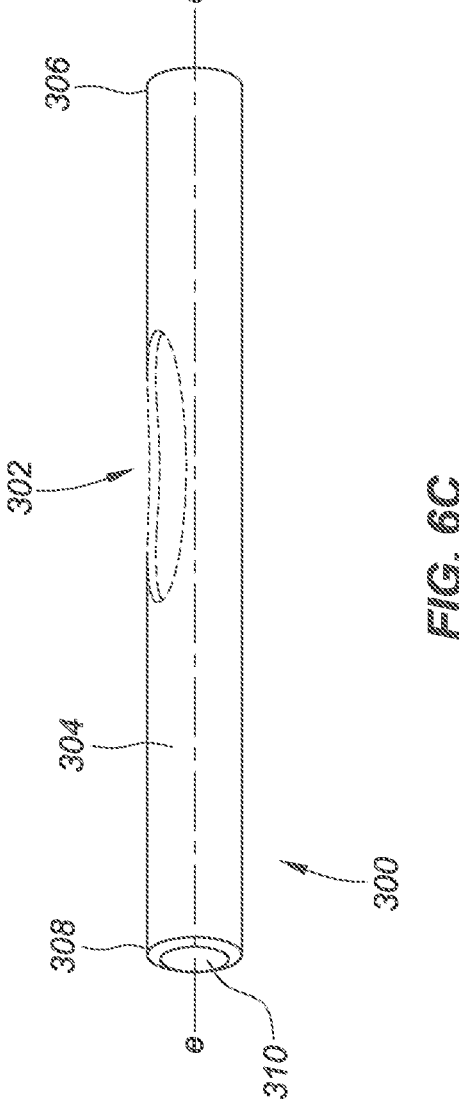
FIG. 6C is an isometric, side, top, and distal end view of a catheter insertion device that includes a depression area, in accordance with embodiments of the present disclosure.

FIG. 6C is an isometric, side, top, and distal end view of a catheter insertion device 300 that includes a depression area 302, in accordance with embodiments of the present disclosure. The catheter insertion device 300 can comprise an elongate shaft 304 that extends along a shaft longitudinal axis ee and further comprises a shaft proximal end 306 and a shaft distal end 308. A shaft inner wall of the elongate shaft 304 can define a shaft lumen 310 extending therethrough. In some embodiments, the catheter insertion device 300 may not have an access lumen, as depicted in FIG. 6A. Instead, the catheter insertion device 300 can include a particular region (e.g., depression area 302 depicted in phantom) that comprises a material with an increased flexibility in relation to material that surrounds the depression area 302. For example, the catheter insertion device 300 can include a depression area 302 that has a reduced wall thickness. The wall of the elongate shaft 304 can have a reduced wall thickness in the particular depression area 302, allowing for a physician to depress the depression area 302 toward the longitudinal axis ee to make contact with a catheter disposed within the catheter insertion device 300 to control the longitudinal movement of the catheter. In some embodiments, the depression area 302 can include a plurality of dimples, where material that forms the elongate shaft 304 is removed. This can increase a flexibility of the depression area 302, allowing a physician to depress the depression area 302 and make contact with the catheter to control the longitudinal movement of the catheter. In some embodiments, the depression area 302 can be formed from a different material than the material that forms the elongate shaft 304. For example, in some embodiments, the depression area 302 can be formed from an elastic material (e.g., rubber), which can be depressed by a physician to make contact with the catheter.

Figure 7:
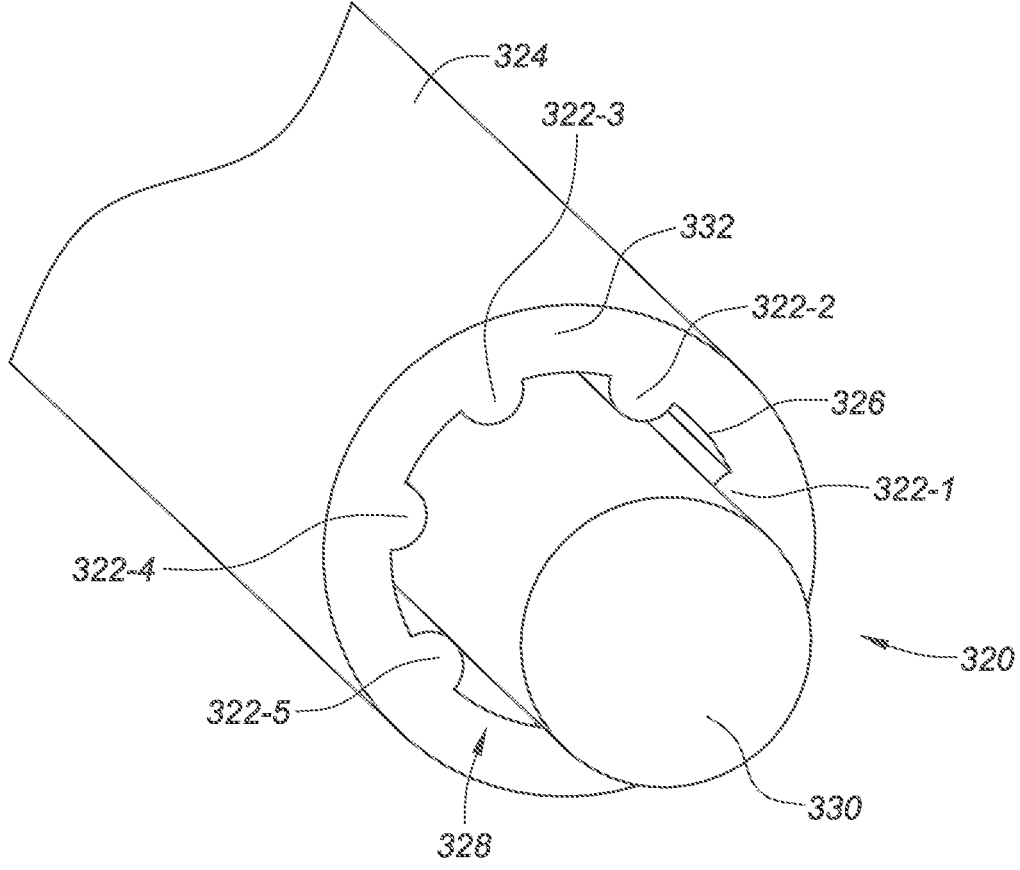
FIG. 7 is an isometric side, top, and distal end view of a catheter insertion device that includes a plurality of longitudinal ridges on a shaft inner wall of the catheter insertion device, in accordance with embodiments of the present disclosure.

FIG. 7 is an isometric side, top, and distal end view of a catheter insertion device 320 that includes a plurality of longitudinal ridges 322-1, 322-2, 322-3, 322-4, 322-5 on a shaft inner wall 326 of the catheter insertion device, in accordance with embodiments of the present disclosure. Hereinafter, the plurality of longitudinal ridges 322-1, 322-2, 322-3, 322-4, 322-5 are referred to in the plural as longitudinal ridges 322. Although five longitudinal ridges 322 are depicted, an additional two longitudinal ridges are hidden from view behind catheter 330, which is disposed within the shaft lumen 328. However, fewer than seven longitudinal ridges 322 or greater than seven longitudinal ridges can be disposed within the catheter insertion device 320. The catheter insertion device 320 can comprise an elongate shaft 324 that extends along a shaft longitudinal axis. The shaft inner wall 326 of the elongate shaft 324 can define a shaft lumen 328 extending therethrough. In some embodiments, the shaft inner wall 326 can include the plurality of longitudinal ridges 322, which can longitudinally extend along a portion of the shaft inner wall 326, parallel with the shaft longitudinal axis. However, in some embodiments, the plurality of longitudinal ridges 322 can be divergent with the shaft longitudinal axis. For example, in some embodiments, the plurality of longitudinal ridges 322 can helically encircle the shaft longitudinal axis. The plurality of longitudinal ridges can extend from a proximal end to a distal end of the elongate shaft 324; from a proximal end of the elongate shaft 324 to a region of the elongate shaft 324 that is located proximal to the distal end of the elongate shaft 324; and/or from a distal end of the elongate shaft 324 to a region of the elongate shaft 324 that is located distal to the proximal end of the elongate shaft 324.

In some embodiments, the plurality of longitudinal ridges 322 can extend from the shaft inner wall 326 radially inward towards a longitudinal axis of the elongate shaft 324. In an example, the shaft inner wall 326 can be indented on either side of each of the plurality of longitudinal ridges 322. The plurality of longitudinal ridges 322 can be circumferentially and equally spaced around the shaft inner wall 326. As depicted, the plurality of longitudinal ridges 322 can be semi-cylindrical in shape; however, the longitudinal ridges 322 can be square shaped, triangular shaped, rectangular shaped, etc.

In some embodiments, the longitudinal ridges 322 can be formed from a material with a pliability that has a greater pliability than that of a shaft wall 332 of the elongate shaft 324. In some embodiments, the longitudinal ridges 322 can be formed from a material that has a durometer in a range from 25 Shore A (25A) to 80 Shore D (80D). In an example, the plurality of longitudinal ridges 322 can create friction between the shaft of the catheter 330 and the catheter insertion device 320. The friction between the shaft of the catheter 330 and the catheter insertion device 320 can prevent unintended longitudinal movement of the catheter 330 with respect to catheter insertion device 320. For instance, as previously discussed, a catheter 330 wanting to return to its natural state when straightened inside the catheter insertion device 320 can have a propensity to move longitudinally either proximally or distally with respect to the catheter insertion device 320. Such movement can be reduced or prevented altogether via the plurality of longitudinal ridges 322.

Figure 8:
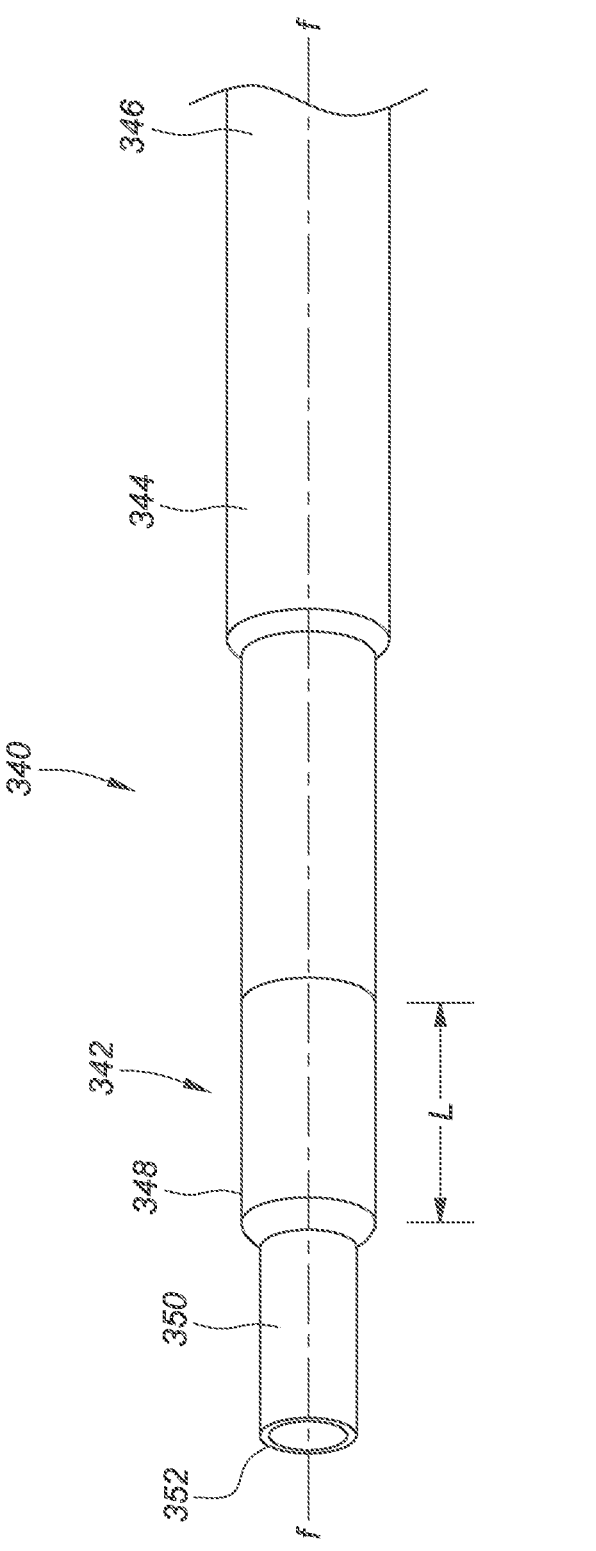
FIG. 8 is an isometric, side, top, and distal end view of a catheter insertion device that includes a tip indicator and a catheter disposed within the catheter insertion device, in accordance with embodiments of the present disclosure.

FIG. 8 is an isometric, side, top, and distal end view of a catheter insertion device 340 that includes a tip indicator 342 and a catheter disposed within the catheter insertion device 340, in accordance with embodiments of the present disclosure. The catheter insertion device 340 can comprise an elongate shaft 344 that extends along a shaft longitudinal axis ff and comprises a shaft proximal end 346 and a shaft distal end 348. FIG. 8 further depicts a catheter 350 that is disposed within a shaft lumen of the catheter insertion device 340. The catheter 350 has been advanced through the catheter insertion device 340, such that a catheter distal end 352 is located distally with respect to the shaft distal end 348.

In some embodiments, the catheter insertion device 340 can include a tip indicator 342 disposed at a distal end of the catheter insertion device 340. The tip indicator 342 can be located along a tip indicator region of the catheter insertion device 340 defined by line gg. In some embodiments, the tip indicator region can be of a different color than an adjacent proximal portion of the elongate shaft 340. In an example, the tip indicator 342 can differentiate the tip indicator region from other portions (e.g., an adjacent portion) of the catheter insertion device 340.

Differentiation between the tip indicator 342 and the other portions of the catheter insertion device 340 can be beneficial when inserting the distal end of the catheter insertion device 340 into a hemostasis valve. In some embodiments, the distal end of the catheter insertion device 340 may need to be inserted through the hemostasis valve, such that the shaft distal end 348 of the catheter insertion device 340 passes all the way through the hemostasis valve into an introducer lumen, as depicted in FIG. 4C. It can be difficult for a physician to determine how far to insert the catheter insertion device 340 through the hemostasis valve to ensure that the distal end 348 of the catheter insertion device 340 is disposed within the introducer lumen. In some embodiments, the tip indicator 342 can serve as a visual indicator that can be referenced to determine how far to insert the distal end 348 of the catheter insertion device 340 into the hemostasis valve. In an example, the distal end 348 of the catheter insertion device 340 can be inserted into the hemostasis valve such that no portion of the tip indicator region is visible, indicating that the distal end 348 of the catheter insertion device 340 is across the hemostasis valve. If any portion of the tip indicator 342 is visible, this can indicate that the distal end 348 of the catheter insertion device 340 is not across the valve. For instance, the tip indicator region can have a length that is equivalent to a longitudinal length of the radially expandable lumen of a hemostasis valve. The longitudinal length of the tip indicator region, defined by line gg, can be in a range from 0.02 to 0.5 inches, in some embodiments. The tip indicator region can be a variety of colors, including but not limited to red, green, yellow, orange, black, white, etc.

Figure 9A:
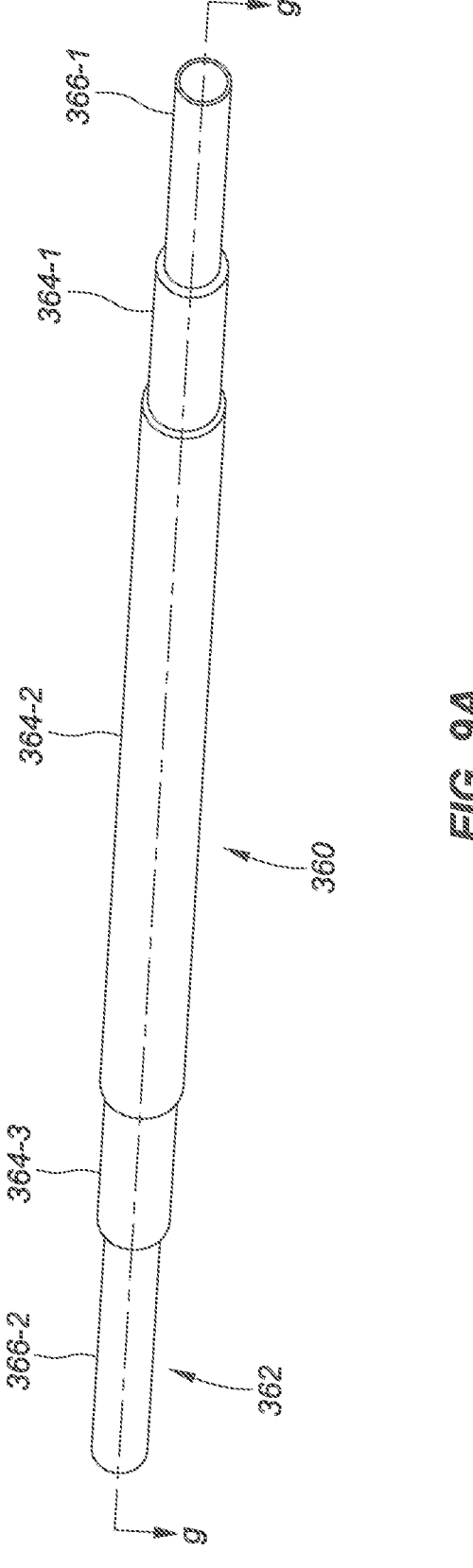
FIG. 9A is an isometric, side, top, and proximal end view of a catheter insertion device with a variable inner diameter and a catheter disposed within the catheter insertion device, in accordance with embodiments of the present disclosure.

FIG. 9A is an isometric, side, top, and proximal end view of a catheter insertion device 360 with a variable inner diameter and a catheter 362 disposed within the catheter insertion device 360, in accordance with embodiments of the present disclosure. The catheter insertion device 360 can comprise an elongate shaft comprising a shaft proximal portion 364-1, a shaft middle portion 364-2, and a shaft distal portion 364-3 that extends along a shaft longitudinal axis gg. The catheter 362 can be disposed within the catheter insertion device 360 and can include a catheter proximal end 366-1 and a catheter distal end 366-2.

In some embodiments, the shaft proximal portion 364-1 can have an outer proximal diameter that is less than an outer middle diameter of the shaft middle portion 364-2. In some embodiments, the shaft distal portion 364-3 can have an outer distal diameter than is less than an outer middle diameter of the shaft middle portion 364-2. In an example, a reduced outer distal diameter can allow for the shaft distal portion 364-3 to be more easily inserted into a hemostasis valve. For instance, the reduced outer diameter of the shaft distal portion 364-3 can allow for the shaft distal portion 364-3 to be inserted into the hemostasis valve using less force due to a reduced surface area associated with the shaft distal portion 364-3.

Figure 9B:
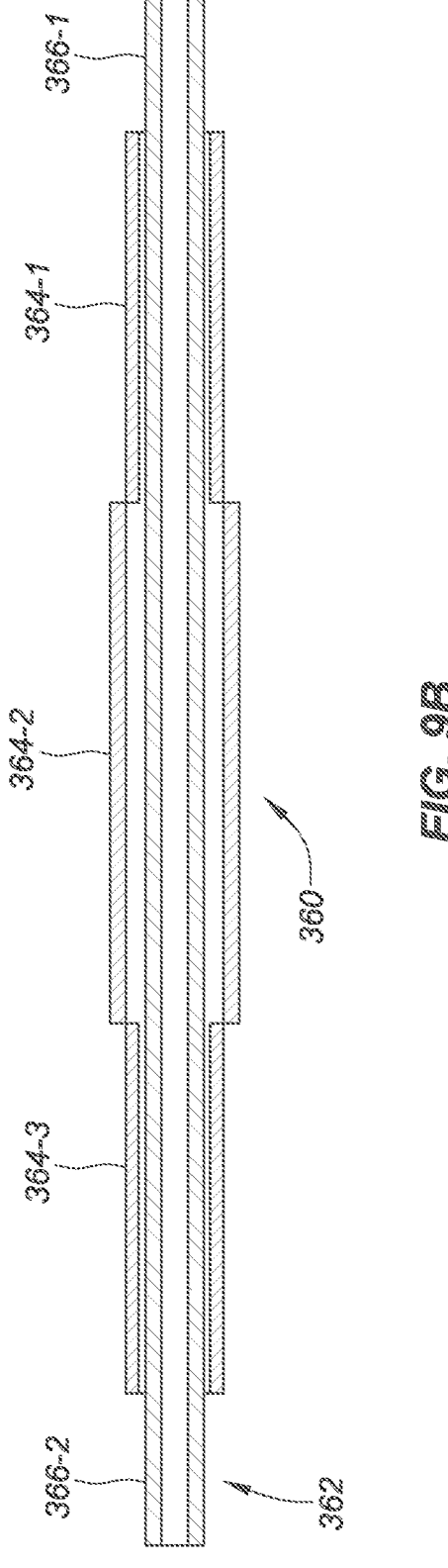
FIG. 9B is cross-sectional side view of the catheter insertion device and catheter depicted in FIG. 9A, along line gg, in accordance with embodiments of the present disclosure.

FIG. 9B is cross-sectional side view of the catheter insertion device 360 and catheter 362 depicted in FIG. 9A along line gg, in accordance with embodiments of the present disclosure. In some embodiments, the shaft proximal portion 364-1 can have an inner proximal diameter that is less than an inner middle diameter of the shaft middle portion 364-2. In some embodiments, the shaft distal portion 364-3 can have an inner distal diameter than is less than an inner middle diameter of the shaft middle portion 364-2. In an example, a reduced inner distal diameter and reduced inner proximal diameter can reduce or eliminate unintentional longitudinal movement of the catheter 362. A curved catheter, once straightened (e.g., via the catheter introducer device 360) can slip from the introducer device 360 if not properly constrained. Limiting the inner diameter of the straightener on both ends of the introducer device 360 can allow for a slip fit of the straightened portion of the catheter 362 at the shaft proximal portion 364-1 and the shaft distal end 364-3. As the catheter tries to return to its natural (e.g., curved) state, a force (e.g., normal force) can be applied to the portions of the catheter 362 disposed in the shaft proximal portion 364-1 and the shaft distal portion 364-3, preventing or limiting an amount of longitudinal movement of the catheter 362 with respect to the catheter insertion device 360. The larger inner middle diameter of the shaft middle portion 364-2 can minimize a potential for permanent curve setting of a curved or tight radiused catheter during the insertion process.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment of a catheter insertion device has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An assembly for inserting a catheter into a blood vessel, the assembly comprising:
   a catheter insertion device comprising a catheter insertion device shaft that defines a catheter insertion device shaft lumen, wherein the catheter insertion device shaft comprises a flexible tip portion and a distal end shaft face;
   a catheter comprising a catheter shaft movably disposed within the catheter insertion device shaft lumen;
   a bleedback valve disposed within the flexible tip portion of the catheter insertion device shaft and configured to inhibit proximal flow of fluid through the bleedback valve and accommodate the catheter shaft through the bleedback valve, wherein the bleedback valve comprises a distal face aligned with the distal end shaft face of the catheter insertion device;
   an introducer comprising an introducer shaft that defines an introducer lumen and configured for insertion into the blood vessel and to accommodate detachable mounting of the flexible tip portion of the catheter insertion device shaft to the introducer to accommodate the catheter shaft into the introducer through the catheter insertion device shaft lumen; and
   a hemostasis valve disposed within a proximal end portion of the introducer and configured to inhibit proximal flow of fluid out of the introducer lumen, wherein the hemostasis valve comprises a radially expandable lumen, wherein, in an inserted configuration, the distal face of the bleedback valve is disposed distal to the radially expandable lumen of the hemostasis valve to cause the distal face of the bleedback valve to be in fluid communication with the introducer lumen prior to insertion of the catheter shaft.

2. The assembly of claim 1, wherein the catheter insertion device shaft comprises longitudinally extending ridges that define at least a portion of the catheter insertion device shaft lumen.

3. The assembly of claim 2, wherein the longitudinally extending ridges have a greater pliability than that of a surrounding portion of the catheter insertion device shaft and extend radially inward from the surrounding portion of the catheter insertion device shaft.

4. The assembly of claim 2, wherein the longitudinally extending ridges are configured to increase a friction between the catheter insertion device shaft and the catheter shaft.

5. The assembly of claim 2, wherein the longitudinally extending ridges helically encircle the catheter insertion device shaft lumen.

6. The assembly of claim 2, wherein the longitudinally extending ridges are circumferentially spaced apart such that portions of the catheter insertion device shaft disposed between the longitudinally extending ridges define a portion of the catheter insertion device shaft lumen.

7. The assembly of claim 1, wherein the bleedback valve comprises an outer circumferential surface and bleedback grooves that extend longitudinally along the outer circumferential surface of the bleedback valve and are configured to accommodate proximal flow of blood past the bleedback valve to provide confirmation of access to a patient's vasculature.

8. The assembly of claim 1, wherein the flexible tip portion of the catheter insertion device shaft has a smaller outer diameter than a proximal end portion of the catheter insertion device shaft.

9. The assembly of claim 1, wherein the catheter insertion device shaft comprises embedded longitudinal reinforcement strips.

10. The assembly of claim 9, wherein each of the embedded longitudinal reinforcement strips is formed of a material with a durometer that is greater than a durometer of a surrounding portion of the catheter insertion device shaft.

11. The assembly of claim 9, wherein the embedded longitudinal reinforcement strips are formed from a polymer material.

12. The assembly of claim 1, wherein the bleedback valve defines a radially expandable lumen that extends longitudinally through a center of the bleedback valve.

13. The assembly of claim 12, wherein the bleedback valve comprises a top lumen wall, a bottom lumen wall, and side lumen walls that form the radially expandable lumen.

14. The assembly of claim 13, wherein the bleedback valve is formed from a silicon rubber.

15. An assembly for inserting a catheter into a blood vessel, the assembly comprising:
   a catheter insertion device comprising a catheter insertion device shaft that defines a catheter insertion device shaft lumen, wherein the catheter insertion device shaft defines an access lumen extending between an inner wall and an outer wall of the catheter insertion device shaft, and an elastic member covering the access lumen to block access to the catheter insertion device shaft lumen through the access lumen, wherein the access lumen and the elastic member are configured to accommodate hand depression of the elastic member to displace an inner surface of the elastic member through the access lumen and into the catheter insertion device shaft lumen;
   a catheter comprising a catheter shaft movably disposed within the catheter insertion device shaft lumen, wherein at least a portion of the catheter shaft is accessible via the access lumen of the catheter insertion device shaft when the catheter is advanced through the catheter insertion device;
   an introducer comprising an introducer shaft that defines an introducer lumen and configured for insertion into the blood vessel and to accommodate detachable mounting of a distal end portion of the catheter insertion device shaft to the introducer to accommodate the catheter shaft into the introducer through the catheter insertion device shaft lumen; and
   a hemostasis valve disposed within a proximal end portion of the introducer and configured to inhibit proximal flow of fluid out of the introducer lumen.

16. The assembly of claim 15, wherein the catheter insertion device shaft comprises longitudinally extending ridges that define at least a portion of the catheter insertion device shaft lumen.

17. The assembly of claim 16, wherein the longitudinally extending ridges have a greater pliability than that of a surrounding portion of the catheter insertion device shaft and extend radially inward from the surrounding portion of the catheter insertion device shaft.

18. The assembly of claim 16, wherein the longitudinally extending ridges are configured to increase a friction between the catheter insertion device shaft and the catheter shaft.

19. The assembly of claim 16, wherein the longitudinally extending ridges helically encircle the catheter insertion device shaft lumen.

20. The assembly of claim 16, wherein the longitudinally extending ridges are circumferentially spaced apart such that portions of the catheter insertion device shaft disposed between the longitudinally extending ridges define a portion of the catheter insertion device shaft lumen.

* * * * *